(12) United States Patent
Pani et al.

(10) Patent No.: US 9,089,734 B2
(45) Date of Patent: Jul. 28, 2015

(54) APPARATUS, A SYSTEM AND A RELATING METHOD FOR LOCAL OR REMOTE REHABILITATION AND FUNCTIONAL EVALUATION OF THE HANDS

(71) Applicant: Universita degli Studi di Cagliari, Cagliari (IT)

(72) Inventors: Danilo Pani, Cagliari (IT); Gianluca Barabino, Sestu (IT); Alessia Dessi, Quartu Sant'Elena (IT); Alessandro Mathieu, Cagliari (IT); Luigi Raffo, Cagliari (IT)

(73) Assignee: UNIVERSITA DEGLI STUDI DI CAGLIARI, Cagliari (IT)

( * ) Notice: Subject to any disclaimer, the term of this patent is extended or adjusted under 35 U.S.C. 154(b) by 267 days.

(21) Appl. No.: 13/754,649

(22) Filed: Jan. 30, 2013

(65) Prior Publication Data
US 2013/0143718 A1    Jun. 6, 2013

(51) Int. Cl.
*A63B 24/00*     (2006.01)
*A63B 21/00*     (2006.01)
(Continued)

(52) U.S. Cl.
CPC ......... *A63B 21/0004* (2013.01); *A63B 21/0023* (2013.01); *A63B 21/00043* (2013.01); *A63B 21/1469* (2013.01); *A63B 23/16* (2013.01); *A63B 2024/0065* (2013.01); *A63B 2024/0068* (2013.01); *A63B 2024/0071* (2013.01); *A63B 2024/0078* (2013.01); *A63B 2024/0096* (2013.01); *A63B 2071/063* (2013.01); *A63B 2071/0625* (2013.01); *A63B 2071/0655* (2013.01); *A63B 2220/56* (2013.01);
(Continued)

(58) Field of Classification Search
CPC ........... A63B 21/0004; A63B 21/0023; A63B 21/1469; A63B 23/16; A63B 24/00
USPC ........... 482/1–9, 44, 45, 900–902; 601/23, 34
See application file for complete search history.

(56) References Cited

U.S. PATENT DOCUMENTS 7,837,599 B2 * 11/2010 Kowalczewski et al. ....... 482/44
2008/0161733 A1 * 7/2008 Einav et al. ..................... 601/34
(Continued)

OTHER PUBLICATIONS

Ludovic Dovat et al., *HandCARE: A Cable-Actuated Rehabilitation system to Train Hand Function After Stroke*, IEEE Transactions on Neural systems and Rehabilitation Engineering, vol. 16, No. 6, Dec. 2008, pp. 582-591.
(Continued)

*Primary Examiner* — Glenn Richman
(74) *Attorney, Agent, or Firm* — Workman Nydegger

(57) ABSTRACT

An apparatus for the local and/or remote rehabilitation and functional evaluation of the right and/or left hand of a user includes: a number of gym tools for the execution of hand exercises, each gym tool including a mechanical part, a sensor for the transformation of measured physical parameters into electrical signals; a user interface, configured to guide the user in the use of the gym tools, and providing feedbacks to the sequence of user actions; a first processing unit, configured to manage the apparatus functions, signal processing, storing and forwarding information on the measured physical parameters to at least one external device; a short-range communication module, configured to allow a real-time close-distance control of the apparatus; a wide-range communication module, configured to allow the connection to at least one long-distance tele-monitoring system.

13 Claims, 22 Drawing Sheets

(51) Int. Cl.
  *A63B 21/002*  (2006.01)
  *A63B 23/16*  (2006.01)
  *A63B 71/06*  (2006.01)

(52) U.S. Cl.
  CPC ....... *A63B2220/58* (2013.01); *A63B 2220/803* (2013.01); *A63B 2225/50* (2013.01)

(56) References Cited

U.S. PATENT DOCUMENTS

2010/0298097 A1* 11/2010 Preumont et al. ................ 482/5

2012/0157263 A1* 6/2012 Sivak et al. ................ 482/4

OTHER PUBLICATIONS

William K. Durfee et al., *Design and Usability of a Home Telerahabilitation System to Train Hand Recovery Following Stroke*, Journal of Medical Devices, Dec. 2009, vol. 3, pp. 041003-1-041003-8.

Tyromotion GmbH, *Pablo Hand Arm Rehabilitation* Brochure, published at least as early as Jan. 15, 2013.

* cited by examiner

APPARATUS, A SYSTEM AND A RELATING METHOD FOR LOCAL OR REMOTE REHABILITATION AND FUNCTIONAL EVALUATION OF THE HANDS

BACKGROUND OF THE INVENTION

1. Field of the Invention

The present invention relates to a computerized apparatus and the related system and method for local or remote rehabilitation or tele-rehabilitation and functional evaluation of hands of patients, in particular for locally or remotely evaluating the patient's progresses and training quality in the process of hand functionality rehabilitation.

In particular the present invention relates to a portable telemedicine apparatus for training and for monitoring active hand rehabilitation exercises, which the patient can autonomously execute at home without any assistance.

2. Description of the Prior Art

Recovering the hand functionality lost or reduced by injuries, interventions and chronic diseases is of particular interest because of the great impairment for the affected patients in their daily life. After the acute phase, when a pharmacological therapy should be properly set up, it is necessary to start a kinesitherapy in order to help patients in recovering their self-sufficiency, self-confidence and independence. Its effectiveness is strongly dependent on the patient's adhesion to the rehabilitation program, which can consist either of passive or active movements, exploiting or not gym tools.

Closely assisting every patient during the rehabilitation, either in person or from remote with video-based telemedicine systems, requires a huge effort, considerable costs and discomfort for the patients, being actually hardly practicable. A tele-rehabilitation system expressly designed for the hand, exploiting a store-and-forward approach with a preliminary data summarization, being able of delivering the rehabilitation services over distance without the need of a synchronization between the caregiver and the patient, can provide significant advantages in terms of costs and benefits for both the patient and the health care service provider.

There is a lack of efficient hand tele-rehabilitation known solutions for patients needing an active kinesitherapy at home, enabling the therapist to evaluate not only the results of the proposed rehabilitation program but also the quality of the patient's training, exercise by exercise.

Most of the known rehabilitation systems are based on gloves or exoskeletons, usually designed for post-stroke recovery through passive movements. In Dovat et al., "Hand-CARE: A cable-actuated rehabilitation system to train hand function after stroke", IEEE Trans. on Neural Systems and Rehabilitation Engineering (2008), cable-driven units connected to each finger by means of soft rings are exploited, being able to move the fingers with predefined patterns (passive movements) and/or to provide a tunable resistance to the hand movement.

Other approaches make use of complex mechanical infrastructures or exoskeletons in order either to assist the movement, or help in restoring the motor function. These systems are usually expensive, not portable and not suitable for patients with hands deformity.

Some commercial systems allow the execution of single hand exercises, usually for evaluation purposes, such as commercial dynamometers for the hand grip strength evaluation. These systems are not designed for clinical training and can't be useful to rehabilitation purposes (usually targeted to one-shot measurements).

Commercial devices, such as Pablo® by Tyromotion GmbH, allow monitoring also the single finger pinch force. Usually the digital versions of these devices are able to provide maximum, average and standard deviation of the applied force, but without any temporal analysis within a series.

Other systems exploit tracking technology to monitor the movements during a rehabilitation session, such as electrogoniometers, as described in Durfee et al., "Design and Usability of a Home Telerehabilitation System to Train Hand Recovery Following Stroke". Journal of Medical Devices (2009), or inertial sensors. These systems can only record the trajectory of the wrists and upper limb movements and usually depends on personal computers which guide the patient in the exercise execution (through an avatar showing the movements to execute or a little game to play) and can eventually manage the transmission of the rehabilitation movements to a medical centre. Also, console games are often used for rehabilitation purposes.

SUMMARY OF THE INVENTION

The aim of the present invention is to provide a computerized apparatus, and the relative system and methods, for the local and/or remote tele-rehabilitation and functional evaluation of the hand, for patients affected by chronic diseases (such as rheumatoid arthritis, scleroderma, etc.) or after an intervention or after ischemic episodes (i.e. post-stroke) and in general in every situation where a proper kinesitherapy and training at the level of the hand is beneficial for the patient. The aim is also that of enabling the use of such an apparatus in two different scenarios, in order to provide different services to the patient and his therapist, overcoming the limitations of current apparatuses and truly opening to the diffusion of tele-rehabilitation.

Another object of the present invention is providing said apparatus with tools, algorithms and methods apt to manage the single exercises informing the patient with the help of visible/audible signals about the progress of the exercise and the whole rehabilitation session. To this aim the apparatus is able to: digitally acquiring the electrical signals coming from the sensorized tools, processing them in real-time in order to pursue delineation (automatic signal segmentation over time), measuring the relevant features of the signal waveform (including time and amplitude parameters), comparing the obtained values with reference ones (if applicable) in order to provide a real-time visible/audible feedback to the patient about the performance achieved in the current/past repetition of the current exercise, computing the running statistics on such features in order to extract a brief summary of the exercise representative of the patient's performance.

Another object of the present invention is providing said apparatus with different communication facilities (both at hardware and software level) to serve at least one of two different addressed scenarios, namely:

(1) the real-time close-distance control of the device, and
(2) the deferred telemonitoring.

Such communication facilities provide no electrical contact with external devices for improved safety and should be energy efficient.

In case (1), the communication means can be an insulated USB connection or preferably a wireless connection, such as Bluetooth, Zigbee, etc. In the preferred embodiment Bluetooth is the choice, and an external Bluetooth module (rather than an embedded one) is preferable for cost/efficacy reasons, since it is required only by the therapist.

In case (2) the communication means is able not only to improve the portability of the apparatus but also to enable an easy and efficient management of the communication costs without special requirements in terms of external tools in the place where the apparatus will be used. In this sense, the communication means should be any of the currently adopted mobile phone technologies such as GSM, GPRS, UMTS, 3G, 4G, etc.

The communication module can be either internal or external, but in the preferred embodiment it is embedded in the main unit of the apparatus (a GSM/GPRS unit), not detachable from it, so that wherever the patient needs to perform the rehabilitation, he has the possibility of doing that autonomously, with controllable connection costs.

In case (1) of real-time close distance control, another object of the present invention is to provide the support hardware/software infrastructure enabling the use of said apparatus in a rehabilitation clinic for training and rehabilitation sessions under the guidance of a therapist, exploiting it in conjunction with a PC. The PC must present the same hardware communication facilities adopted on the apparatus (in the preferred embodiment a Bluetooth module) and runs a graphical user interface enabling the selection of the exercise to be performed, and the associated parameters (e.g. number of repetitions, left or right hand), and providing visualization means for both the aforementioned running statistics computed on the apparatus and the raw signals coming from the sensor in use.

In such a context of case (1), another object of the present invention is to provide the real-time outpatient clinic software application enabling the therapist to perform such operations within a user-friendly graphical environment.

In such a context of case (1), another object of the present invention is to provide a method the therapist can deploy for performing the training and quantitative evaluation of the patient when directly controlling the apparatus.

In case (2) of deferred telemonitoring, another object of the present invention is to provide the support hardware/software infrastructure enabling the use of said apparatus as a tele-rehabilitation device, autonomously used by the patient at home, completely self-contained and stand-alone (i.e. not requiring any additional hardware tools), propagating by a store-and-forward approach to the therapist's PC the essential information about the patient's performance in every rehabilitation session. To this aim, the apparatus is opportunely loaded with a programmed rehabilitation protocol remotely upgradable. In this context a rehabilitation protocol consists of the set of exercises to be performed, their order, the associated threshold levels, the hand to use, the number of repetitions, the number of series, which should be appropriately chosen depending on the patient's needs. Another object of the present invention is to provide audible/visible feedback to guide the user throughout the rehabilitation session. The latest update of the running statistics about the measured features for every exercise are stored in a local memory inside the apparatus in order to send them as a unique summary at the end of the whole rehabilitation session, without any user intervention, to a remote server over the internet exploiting the aforementioned connection means. In this case, the raw data coming from the sensors are neither stored nor transmitted.

In such a context of case (2), another object of the present invention is to provide a whole telemedicine infrastructure including:

1. A server for receiving the connections from the apparatuses assigned to the different patients, storing the retrieved information (summary of the rehabilitation session) in a database and contemporarily sending to the connected apparatus the upgrade of the rehabilitation protocol as defined by the therapist.
2. A server for receiving queries aimed at accessing the database for the deferred retrieval of patients' data and successive analysis by the therapist. The server also accepts from the therapist's client application upgrades on the rehabilitation protocol for specific patients in order to be able of personalizing the kinesitherapy on the evidences of the deferred monitoring.
3. A deferred monitoring application running on a PC that can be used by the therapist in order to evaluate the compliance of the patients to the assigned protocol, visualize the history of the patient in terms of performance (graphical view of the trends in the archived features), analyze the achieved results, modify and upgrade the rehabilitation protocol for a specific patient.

In such a context of case (2), another object of the present invention is to provide a method the therapist can deploy for performing the quantitative evaluation of the patient's rehabilitation when deferred telemonitoring is used.

Preferably, the system is composed of a tele-rehabilitation apparatus, an internet server, a client application for the therapist for remotely evaluating the patient's progresses and training quality, and an outpatient clinic software application for controlling the apparatus in real-time when both the therapist and the patient are in the same place. The system is fully scalable in the number of rehabilitation tools in use and client applications. The rehabilitation apparatus is composed of a number of sensorized gym tools enabling the patient to perform specific rehabilitation exercises for training hand/finger dexterity and strength. It is able of guiding the patient in the rehabilitation session, extracting in real-time the relevant exercise features (amplitudes, times, etc) for providing both a summary of their statistics at the end of the rehabilitation session and audio/visual feedbacks to the patient at run-time. The summary is automatically sent to the internet server through a wireless connection for deferred analysis by the therapist who can retrieve the data and analyze them thanks to its client application. A different wireless connection and an outpatient clinic software application allow controlling the apparatus in real-time from a PC for outpatient rehabilitation, providing additional information to the therapist that would be overwhelming in a tele-rehabilitation context.

According to an aspect of the present invention it is provided an apparatus for the local and/or remote rehabilitation and functional evaluation of the right and/or left hand of a user, the apparatus comprising:

a number of gym tools for the execution of hand exercises, each gym tool including a mechanical part, a sensor for the transformation of measured physical parameters into electrical signals;

a user interface, configured to guide the user in the use of said gym tools, and providing feedbacks to the sequence of user actions;

a first processing unit, configured to manage the apparatus functions, signal processing, storing and forwarding information on said measured physical parameters to at least one external device;

a short-range communication module, configured to allow a real-time close-distance control of the apparatus;

a wide-range communication module, configured to allow the connection to at least one long-distance tele-monitoring system.

According to another aspect of the present invention it is provided a system for the local and/or remote rehabilitation and functional evaluation of the right and/or left hand of a user, the system comprising an apparatus comprising:

a number of gym tools for the execution of hand exercises, each gym tool including a mechanical part, a sensor for the transformation of measured physical parameters into electrical signals;

a user interface, configured to guide the user in the use of said gym tools, and providing feedbacks to the sequence of user actions;

a first processing unit, configured to manage the apparatus functions, signal processing, storing and forwarding information on said measured physical parameters to at least one external device;

a short-range communication module, configured to allow a real-time close-distance control of the apparatus;

the system also comprising at least one second processing unit, in said at least one external device, configured to interact with said short-range communication module, for said real-time close-distance control of the apparatus.

According to a further aspect of the present invention it is provided a system for the local and/or remote rehabilitation and functional evaluation of the right and/or left hand of a user, the system comprising at least one apparatus comprising:

a number of gym tools for the execution of hand exercises, each gym tool including a mechanical part, a sensor for the transformation of measured physical parameters into electrical signals;

a user interface, configured to guide the user in the use of said gym tools, and providing feedbacks to the sequence of user actions;

a first processing unit, configured to manage the apparatus functions, signal processing, storing and forwarding statistical information on said measured physical parameters to at least one external device;

a wide-range communication module, configured to allow the connection to at least one long-distance tele-monitoring system; the system also comprising said at least one long-distance tele-monitoring system, on turn comprising:

at least one server configured to store said statistical information on said measured physical parameters;

at least one second processing unit, in said at least one external device, configured to interact with said at least one server, for said long-distance tele-monitoring.

According to a still further aspect of the present invention it is provided a method for the local and/or remote rehabilitation and functional evaluation of the right and/or left hand of a user, the method comprising the steps of:

providing a number of gym tools for the execution of hand exercises, each gym tool including a mechanical part, a sensor for the transformation of measured physical parameters into electrical signals;

providing a user visual interface, configured to guiding the user in the use of said gym tools, and providing feedbacks to the sequence of user actions;

performing a first processing, to manage the functions of the gym tools, signal processing, storing and forwarding information or statistical information on said measured physical parameters to at least one external device;

performing a short-range communication, to allow a real-time close-distance control of the method;

performing a wide-range communication, to allow the connection to at least one long-distance tele-monitoring system.

A number of advantages are achieved by means of the present invention, including but not limited to, the following features:

Fully integrated, offering on the same apparatus the complete tool set for a rehabilitation session.

Stand alone, in order to avoid any additional external tool at the patient's home, neither a PC.

Installation free approach and true portability (self-contained, battery-powered for several days cordless operation, communicating through the mobile telephone service).

Embedded real-time processing of the signals coming from the sensorized gym tools, i.e. the possibility of providing an interactive experience with the device, with real-time feedback to the patient on the performance during the exercise execution.

Easy to use and low cost, for a widespread adoption even on patient who are not accustomed to PCs and advanced electronic equipment.

Real-time external control, i.e. the possibility for the therapist/physician of controlling the apparatus in real time in an outpatient clinic through a PC.

Deferred telemonitoring, i.e. the possibility for the patient of using the device autonomously at his home, following a preloaded (and remotely upgradeable) sequence of exercises.

Store-and-forward of the rehabilitation summary, in order to avoid communicating overwhelming information difficult to manage by the therapist.

BRIEF DESCRIPTION OF THE DRAWINGS

For a better understanding of the invention, examples of embodiments of the invention are described in the following, which shall be considered only as non-limiting examples, in connection with the attached drawings wherein:

FIG. 22 shows an exemplary embodiment of the block diagram of the software structure of the server application of the present invention;

FIGS. 23 to 29 show exemplary embodiments of displaying windows of results of the tele-rehabilitation method of the system of the present invention;

The same reference numerals and letters in the figures designate the same or functionally equivalent parts.

DETAILED DESCRIPTION OF THE PREFERRED EMBODIMENTS

In the following exemplary non-limiting examples of embodiments of the apparatus and system of the invention are described, with reference to different kinds of features of the same.

Hardware High Level

In an exemplary embodiment, the apparatus of the present invention includes a number of gym tools for the hand preferably packaged in a portable briefcase or similar, allowing the monitoring and training of a set of dynamic and isometric rehabilitation exercises enhancing dexterity and strength. Each gym tool includes a mechanical part, a proper sensor for the transformation of the measured physical parameter into an electrical signal and a connection means. In this manner, the acquired data can be digitalized and real-time processed according to the signal waveform. Each tool can be used alternatively with both hands.

All the gym tools can be housed in the structure which controls and manages their operation.

Figure 1:
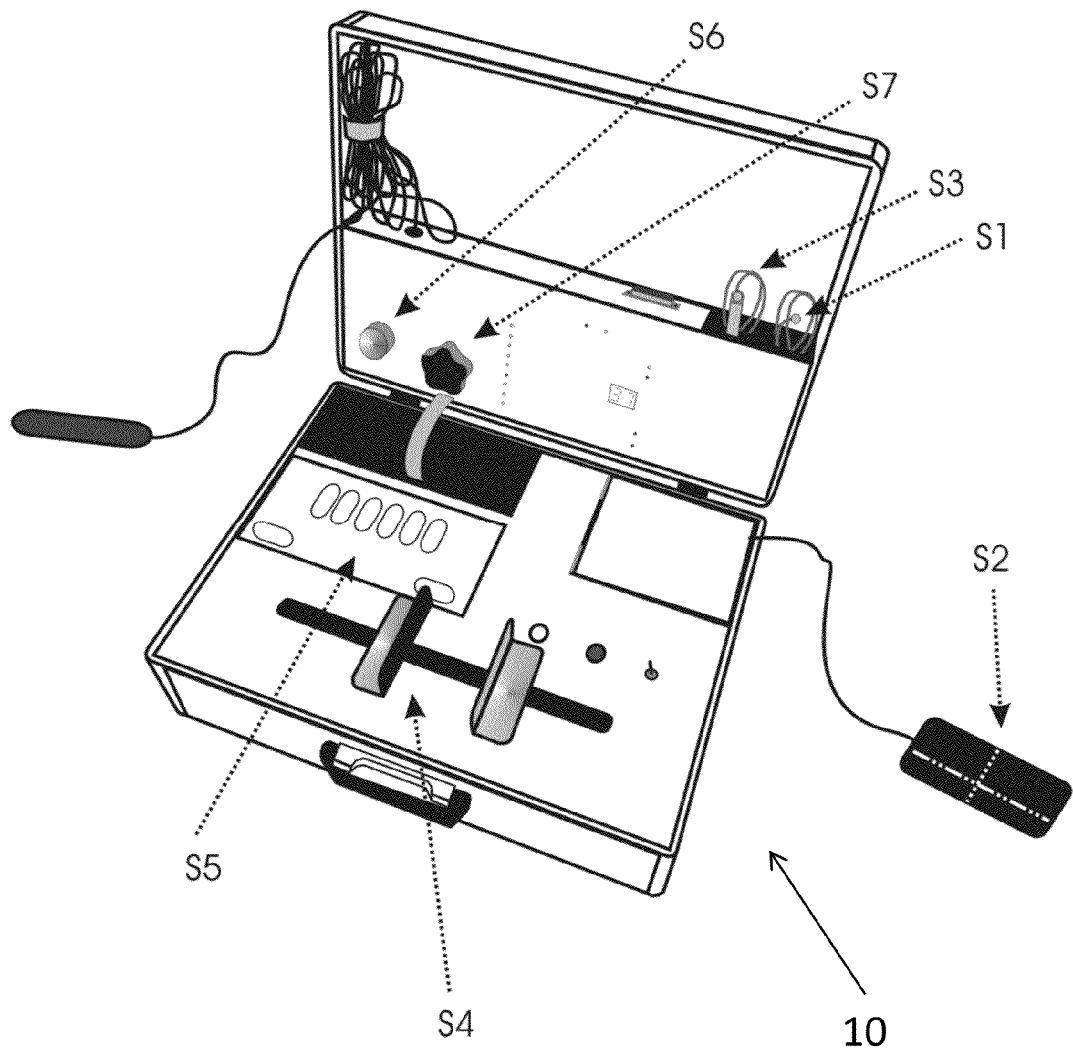
FIG. 1 shows an exemplary embodiment of the apparatus of the present invention.

An exemplary embodiment of the apparatus 10 (FIG. 1) includes preferably:
  A temperature sensor (S1)
  An hand dynamometer (isometric exercise) (S2)
  A gym tool for the identification of the pinch strength of each finger in opposition to the thumb (isometric exercise) (S3)
  A gym tool for the identification of the lateral extension (thumb-little finger) of the hand on a plane (dynamic exercise) (S4)
  A gym tool for the identification of the hand agility when executing a specific sequence of touches on a plane, as finger tapping (dynamic exercise) (S5)
  A gym tool for the identification of the hand agility when rotating a handle without using the wrist (dynamic exercise) (S6)
  A torque meter for the identification of the hand torque when rotating a fixed handle without using the wrist (isometric exercise) (S7)

Figure 2:
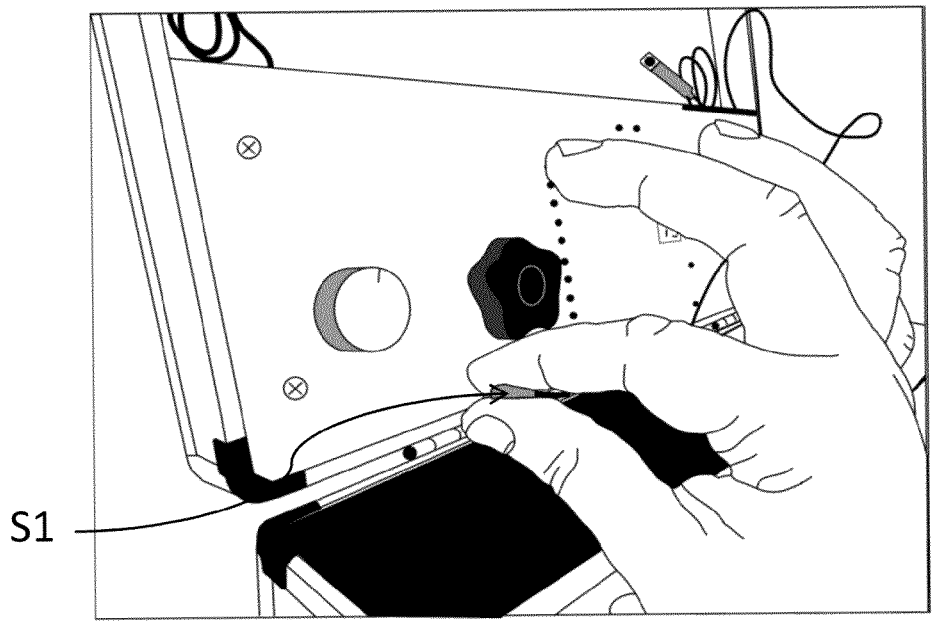
FIGS. 2 to 10 show examples of use of the tools of the apparatus of the present invention.

The temperature sensor (S1) allows the measurement of the fingers temperature before and after the rehabilitation. In a possible embodiment a commercial skin contact temperature probe (as the King-Med YSI skin temperature probe model T0175AU), wired to the whole apparatus, can be used to measure the fingers temperature before and after the rehabilitation session, holding the probe between the thumb and the first finger as depicted in FIG. 2.

Figure 3:
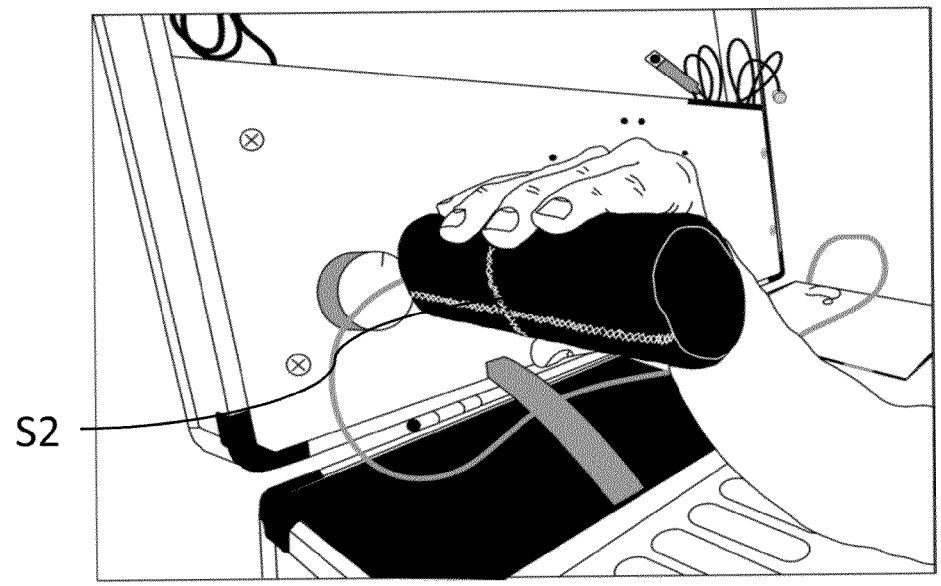
Figure 4:

The hand dynamometer (S2) allows the identification of the hand pinch and grip strength (isometric exercise). A possible low-cost version of this tool can be realized through two hinged halves of a solid handle which presses a commercial Flexiforce A201 force sensor (force range of 0-100 lb (440N)). The said sensor has a linear conductance which increases as the force increases. In a preferred embodiment the handle has an external covering with a drawing showing how to grasp the handle so that the hand correctly exercises the strength on the sensor, avoiding shearing stress. The different ways of holding the handle allow the evaluation of the pinch (FIG. 3) and grip (FIG. 4) force respectively.

Figure 5:
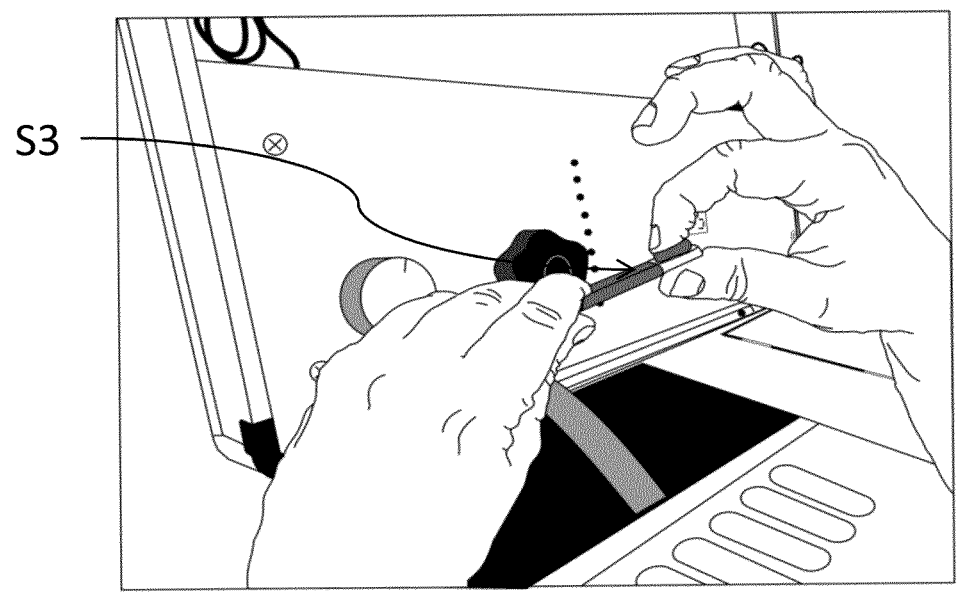

In a preferred embodiment the gym tool for the identification of the pinch strength of each finger in opposition to the thumb (S3) consists of a solid plate (e.g. aluminum) with a force sensor, which can be hold in one hand when exercising the other one, as showed in FIG. 5. In an exemplary realization the force sensor is a commercial Flexiforce A201 sensor (force range of 0-25 lb (110N)), which increases its conductance linearly as the applied force increases. The sensible area of said sensor can be pressed through two silicon pads. In an preferred realization the tool is wired to the apparatus.

Figure 6:
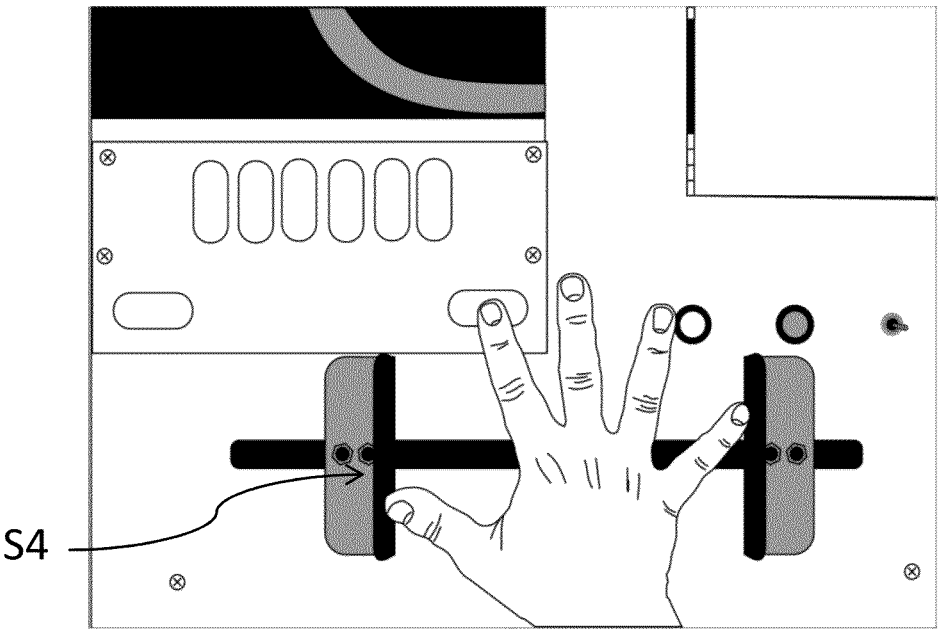
Figure 7:
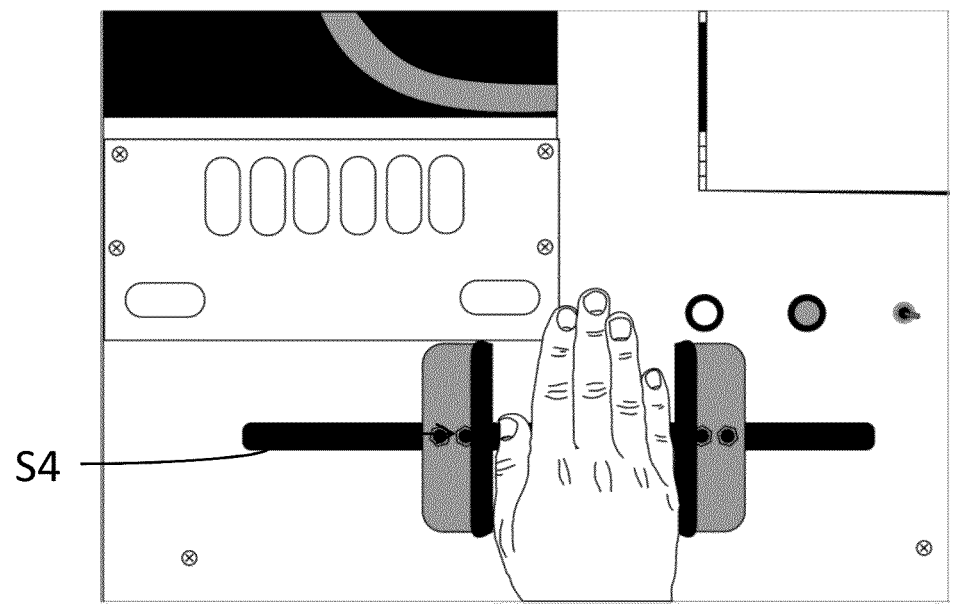

The gym tool for the identification of the lateral extension (thumb-little finger) of the hand on a plane (S4) can exploit a wire position sensor. This tool allows to evaluate the patient's hand extension on the plane when rhythmically opening (FIG. 6) and closing (FIG. 7) the hand. In a preferred embodiment it consists of a moving metal structure, made of two exposed L shaped profiles fixed on two rollers (e.g. the CES-30-00-ZZ by Rollon) able to linearly move on a guide (e.g. a part of a TES03-1040), and an analogue commercial draw wire position sensor offering little unwinding resistant force (e.g. the LZ-PA-15 by Unimeasure) mounted on one of them (while the wire end is fixed to the other). In an exemplary embodiment, this tool is set into the structure of the apparatus, which is used as a support, as shown in FIG. 7.

Figure 8:
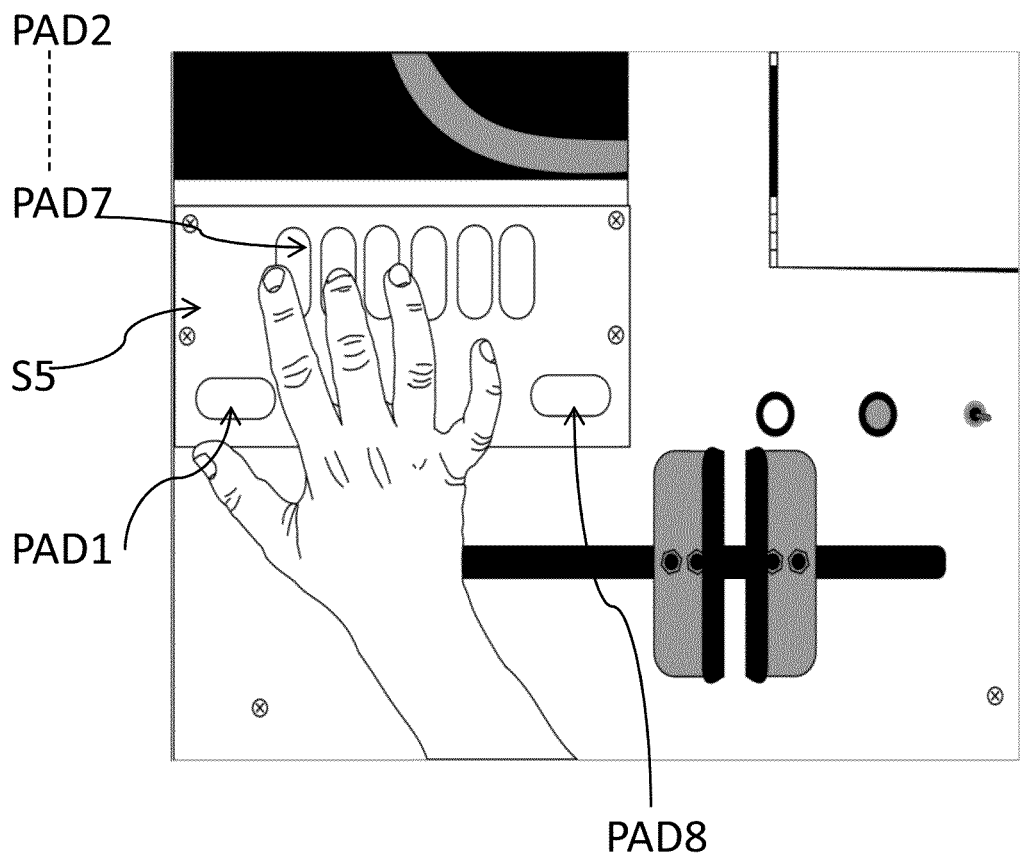
Figure 12:
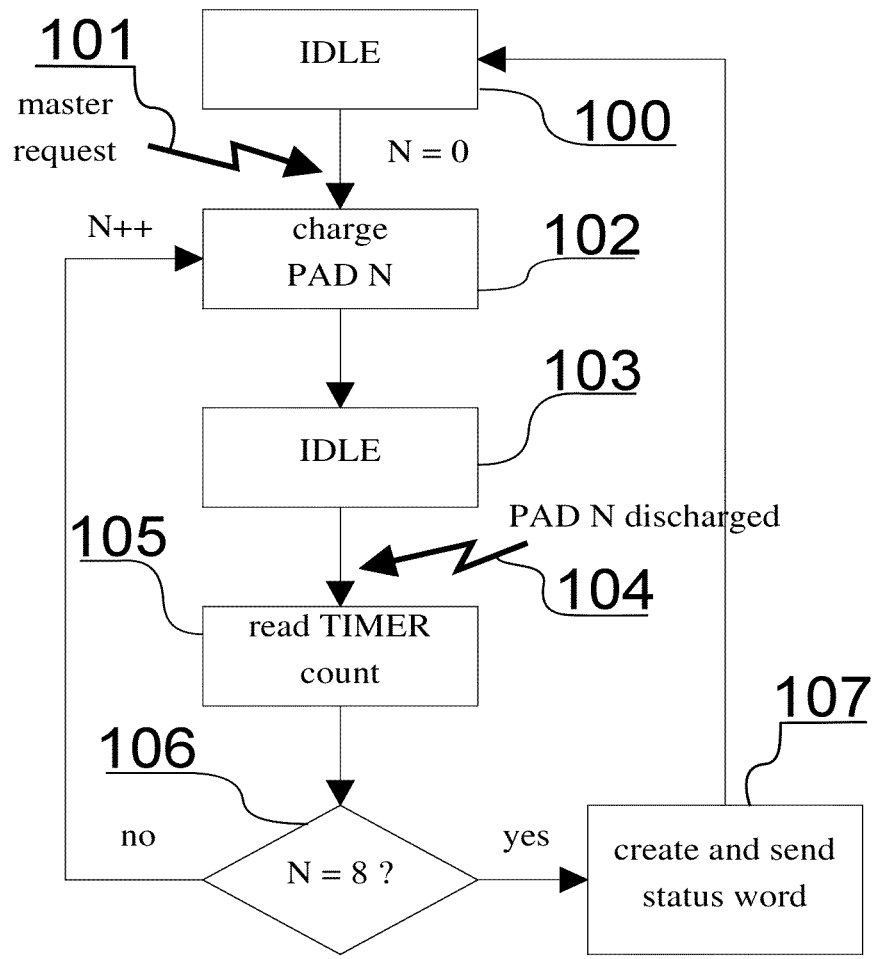
FIGS. 12, 15, 16 show exemplary embodiments of the flow charts of the low level firmware of the apparatus of the present invention.

The tool for the identification of the hand agility when executing a specific sequence of touches on a plane (S5) includes a sensor able to identify fingers touching the plane (FIG. 8). In a preferred embodiment, the said tool consists of a capacitive touch board able to provide a detection of the touch without any counter-resistance from the measuring device. In a preferred embodiment the said tool avoids any direct current injection in the patient's hand. In an exemplary realization, the touch board is based on a low-power microcontroller, managing the reading of the capacitance associated to 8 key-shaped sensible areas on a PCB (PAD 1 . . . 8). The keys form a capacitor with the ground plane surrounding them, and can be sequentially charged by the MCU (FIG. 13), which is able to measure the discharge time. Since the effect of touching a pad is the increase of the capacitance value, it is possible to detect whether a sensor is touched or not comparing the measured discharge time with the base value obtained when the pad is untouched. Whenever required, the device provides over a serial bus (e.g. an I2C one) the current status of the keys in a single byte: the interpretation of the data in the light of the exercise to execute is up to the main processor firmware. The device is set into the structure of the apparatus, which is used as a support. In a preferred embodiment, the layout of the board is designed in order to accommodate both left and right-handed exercises and different hand sizes and postures, as showed in FIG. 8. The low level firmware (described later in more details) loaded onto the microcontroller hosted on the PCB takes care of managing both the scan of each sensible area present and the measurement of the time associated to each charge or discharge cycle performed during the scan. In the preferred embodiment, FIG. 12, the firmware lets the microcontroller stay in its IDLE state until a request from the I2C bus master is received. The request triggers the scan of each sensible area (charge PAD N) and the measurement of the associated discharge time (read TIMER count). Consequently a status word is created by setting high the bits corresponding to the PADs where a touch is detected. The status word can be then forwarded over the I2C bus. The firmware hence enters again the IDLE status, waiting for a new request from the I2C master.

Figure 9:
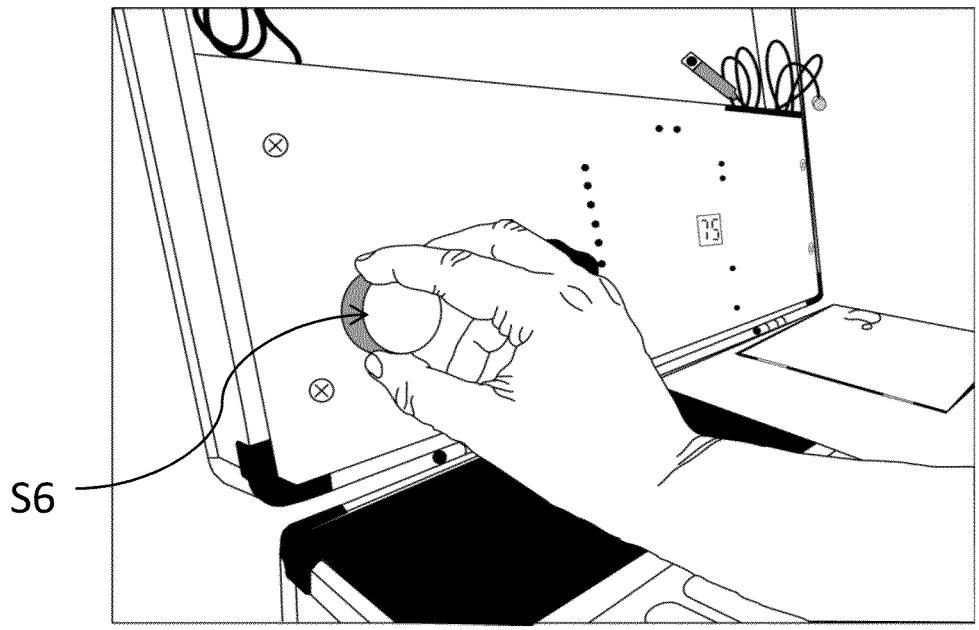

The tool for the identification of the hand agility when rotating a handle without using the wrist (S6) can exploit the use of an angular position sensor. In a preferred embodiment this device consists of a commercial multi-turn (10 turns) precision potentiometer opposing a torque <0.01 Nm fixed to the structure of the apparatus and linked to an aluminum knob which the patient must rotate with his fingers, allowing the identification of the hand rotation speed, while keeping the wrist firmly on the horizontal plane of the apparatus (FIG. 9). The resistance varies linearly with the rotation of the knob so that the voltage measurement on the wiper allows to detect the angular position at any instant. In a preferred embodiment this tool is set into the structure of the apparatus, which is used as a support, mounted on the vertical panel so that the patient can easily rotate the handle holding the wrist on the horizontal plane, as shown in FIG. 9.

Figure 10:
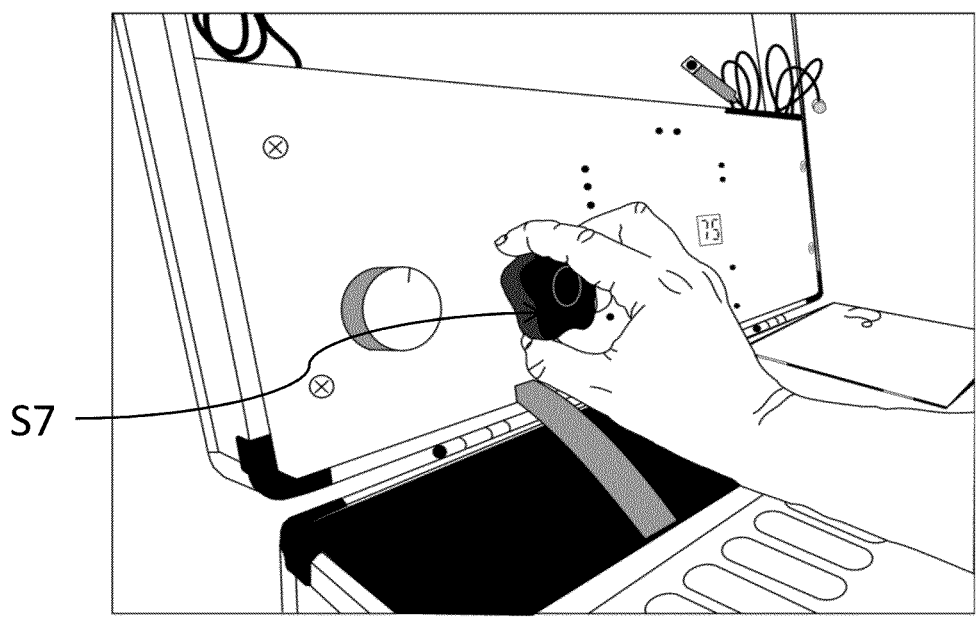

The torque meter for the identification of the rotation torque when rotating a fixed handle with the fingers without using the wrist (S7), can exploit the use of a torque sensor or a force sensor. In an exemplary low-cost embodiment this tool is composed of a 5-lobe 50 mm plastic knob able to slightly turn on its own axis pulling along with it a T bar nut able to press one of two thin-film force sensors (e.g. Tekscan Flexi-Force A201, max 110N), for clockwise and anticlockwise rotations. These sensors linearly vary their conductance in response to the applied force. Thanks to the aforementioned design, the knob cannot spin. In a preferred embodiment this tool is set into the structure of the apparatus, which is used as a support, mounted on the vertical panel, as shown in FIG. 10, so that the patient can easily apply a torque on the handle holding the wrist on the horizontal plane.

The apparatus allows the patient to carry out complete hand rehabilitation training sessions autonomously and easily, by means of a simple user interface, aimed at guiding him throughout the training sessions and providing an intuitive feedback to his actions, possibly integrated into the apparatus. Such a user interface is realized in an intuitive way, allowing also the users not accustomed with advanced electronic devices to understand it easily. In a preferred embodiment, it includes a set of LEDs which show the user the exercise to execute (P1 in FIG. 11), the hand to use (P2 in FIG. 11) and the series of repetitions to perform (P3 in FIG. 11). Also, the apparatus can include a led (P4 in FIG. 11) giving a time reference blinking at 1 Hz (useful for sustained position tests) and a low-battery indicator (P5 in FIG. 11). The visual interface is completed with a 7-segments display in order to display numbers (P6 in FIG. 11). More complex visual apparatuses could also be considered, for example based on LCD displays or led bars. The apparatus can be also provided with a buzzer which chimes to provide audible feedbacks to the patient. In order to obtain the same functionalities and to allow also delivering a more complex audible feedback (such as a synthesized voice) also one or more speakers can be employed, provided that the driving circuitry is also included in the apparatus. Other feedbacks can also be provided, for example with a vibrating device in the main unit or in the specific tool or by more advanced implementations involving tactile feedback elements, for example exploiting haptic technologies. For the patient to interact with the apparatus also an on-off switch (P7 in FIG. 11) and two buttons are present, the first to start the exercise when the patient is ready (P8 in FIG. 11) and the other to skip a single repetition of an exercise (P9 in FIG. 11) or a whole series by pushing the same button for more than two seconds.

Figure 11:
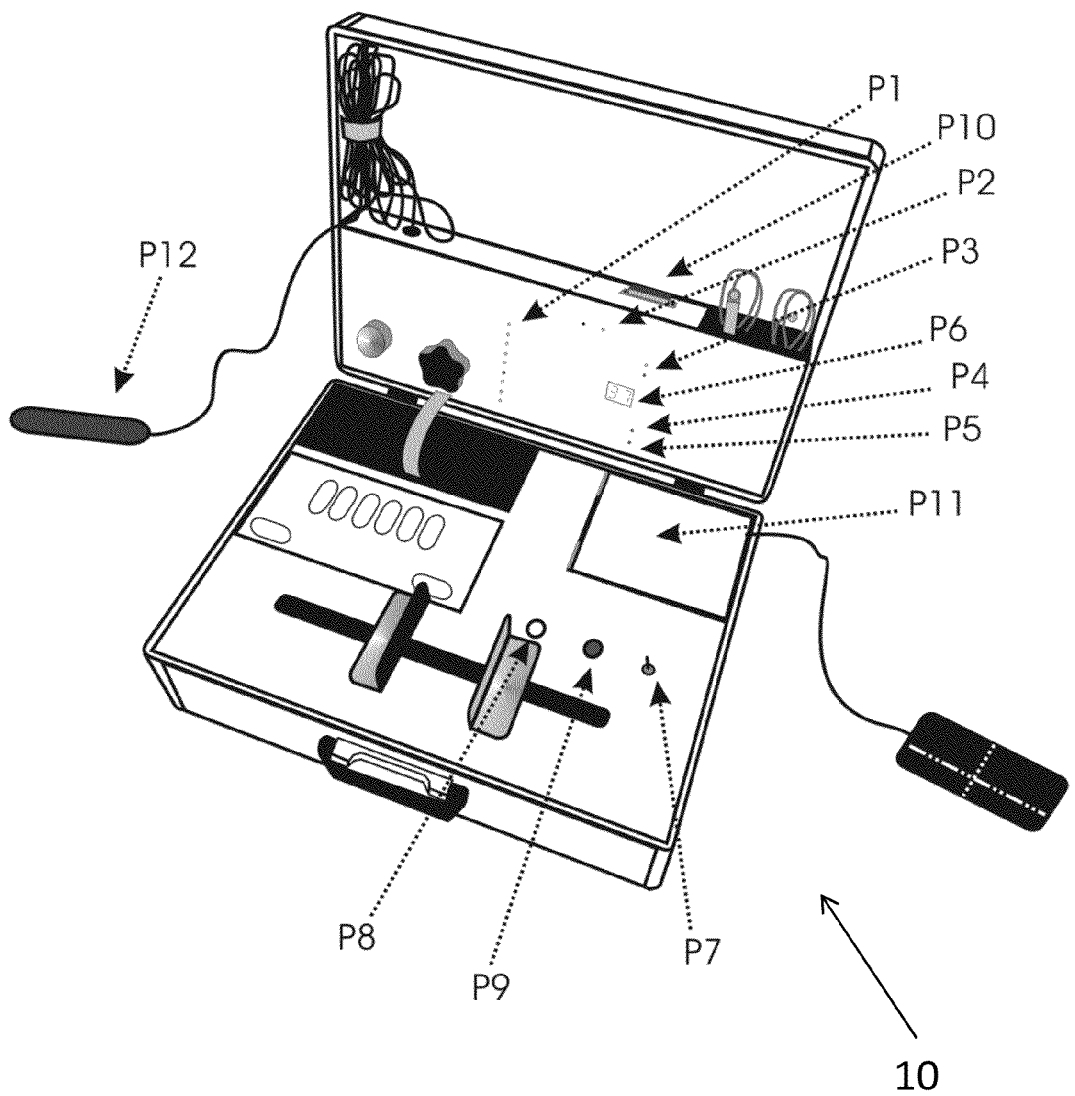
FIG. 11 shows further details of the exemplary embodiment of the apparatus of the present invention.

In a preferred embodiment, the apparatus also includes a programming and communication port (P10 in FIG. 11) providing a clean way to connect an external Bluetooth module and to connect an external programmer to the JTAG ports of the 2 MCUs embedded in the apparatus to program them; a compartment is also present for the hand pinch and grip device and the battery charger (P11 in FIG. 11).

Hardware Low Level

Figure 13:
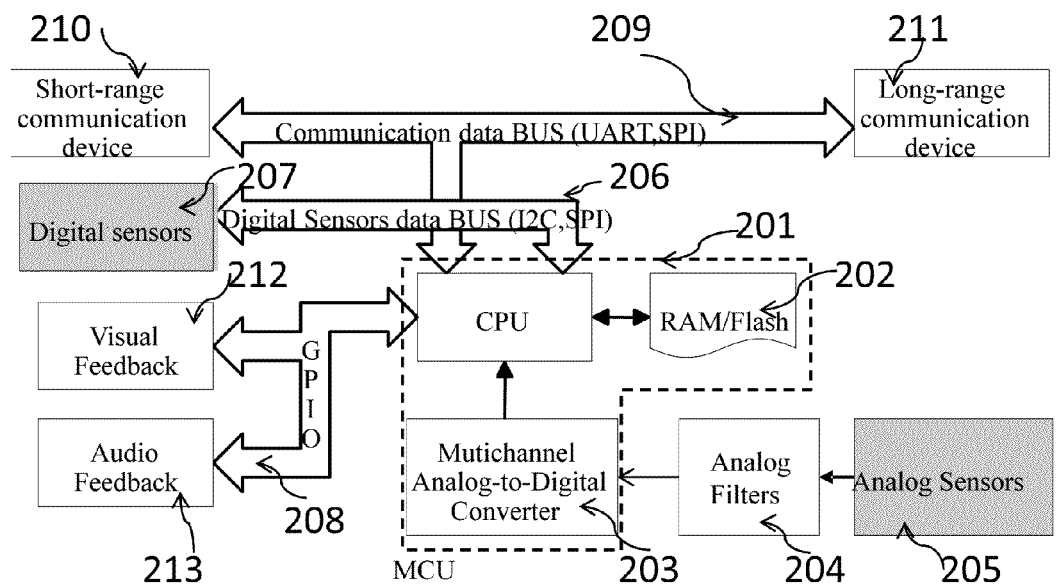
FIGS. 13, 14 show exemplary embodiments of the low level hardware of the apparatus of the present invention.
Figure 14:
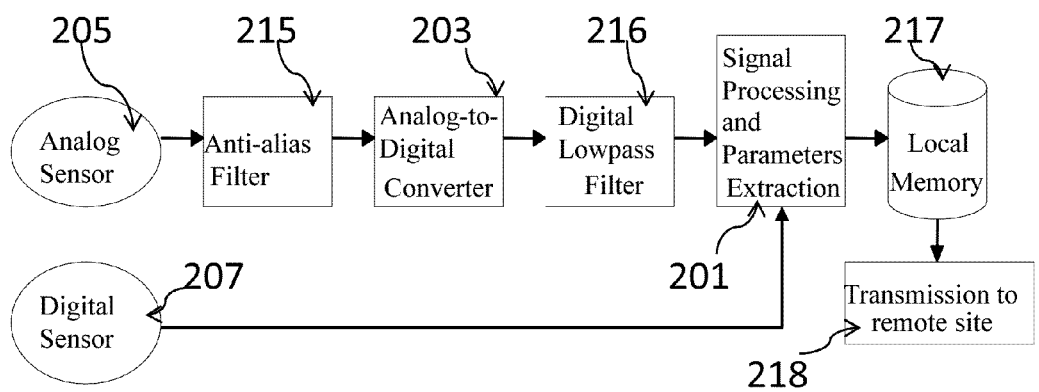

At a low level the hardware of the apparatus comprises a set of sensors apt to detect variations of interesting features which can be exploited to characterize the execution of rehabilitation exercises (FIG. 13). In a possible implementation angle, distance, force, temperature, torque, touch sensors can be employed. Both digital (207) and analog (205) sensors can be used in the apparatus. In case of digital sensors (207), provided that they supply the useful signal in a digital format, over a standard communication port (206) (i.e. SPI, I2C), they are directly interfaced to the main control unit (201). When analog sensors (205) are employed, the signal coming from these must be properly conditioned prior to digital conversion. To this aim a signal conditioning stage is required, able to bias the sensors if necessary and to perform the pre-processing tasks such as anti-alias filtering, noise removal filtering and amplification, required to obtain useful analog signals to be fed to the analog-to-digital conversion stage (ADC). In an example of embodiment (FIG. 14) it includes anti-alias filtering 215, digital low-pass filtering 216, prior to signal processing and parameter extraction performed in the main control unit 201, and storage in the local memory 217 and subsequently transmitted remotely 218.

In a preferred embodiment, NTC thermistor sensors (such as the King-Med YSI skin temperature probe model T0175AU, YSI400 compatible) can be used to measure the fingers temperature (S1), with resistance values decreasing as the temperature increases. Although their non-linear characteristic, these sensors are particularly suitable for the temperature range of the human skin. Also, they don't require a specific calibration procedure, since their calibration chart is interchangeable. In a possible configuration, they are inserted in the feedback line of a non-inverting operational amplifier with a constant input. In this way the output voltage is proportional to the resistance value and the interpolating Steinhart-Hart equation can be used to obtain the temperature value. In a preferred embodiment this estimation is computed by the real-time monitoring software (operating mode (1)) or by the tele-rehabilitation application software (operating mode (2)), allowing a better resolution of the obtained logarithmic values.

In a preferred configuration, all the force sensors of S2, S3 and S7, with a conductance linearly increasing as the force increase, are inserted between the ground and the inverting input of a non-inverting operational amplifier. By using a constant input, the output voltage is proportional to the sensor conductance.

In a preferred embodiment, the position sensors of S4 and S6 are inserted in a voltage divider, with the wiper connected to the input stage of a non-inverting operational amplifier, so that the output voltage is proportional to the input voltage present at the wiper.

In a preferred embodiment, all the non-inverting operational amplifier are provided with a single pole RC net to low-pass filter the input signals before their digital conversion, according to the chosen sampling frequency.

The signal conditioning stage (204) outputs are connected to the ADC (203) inputs. In a preferred embodiment a multi-channel ADC (203) is used, allowing to connect each conditioning stage output to a single ADC input. In different embodiments where fewer ADC input channels are available, a multiplexer can be used to connect the selected outputs to the ADC inputs.

The apparatus comprises an analog to digital converter (ADC) (203), which takes care of digitizing the signals coming from the analog sensors. In a preferred embodiment the ADC can be embedded in the main processing unit (201). The sampling frequency at which the ADC operates can be configured depending on the application and the signal conditioning stage design. For a typical hand rehabilitation scenario a sampling frequency in the range of a hundred of Hz is acceptable. In a possible implementation for example the cut-off frequency of the anti-alias filters (204) could be set to 48 Hz to partially filter out the mains noise, while the sampling frequency could be set to 150 Hz, in order to obtain a sufficient time-resolution.

The operation of the proposed invention is managed by a main processing unit, preferably a low power microcontroller MCU (201). The main processing unit takes care of both general resource management and running signal processing routines aimed to extract useful characteristics of the execution of rehabilitation exercises. In order to fulfill these tasks it must preferably include:

- a sufficient number of general purpose input-output ports (208), apt to route the control signals towards the other units in the apparatus and to manage the said patient feedback devices (212, 213), such as audio and visual feedback devices.
- a sufficient amount of internal memory (202), capable of storing the internal firmware and the intermediate results of the signal processing
- standard communication ports (206, 209), necessary to provide adequate interfaces towards the external digital devices such as digital sensors and communication devices.

In order to communicate with external devices such as the therapist's PC or a server computer, additional devices apt to provide both a short-range (210) and a wide-range (211) connectivity must be employed. In a preferred embodiment these links could be implemented via wireless technologies in order to improve the device usability. For example the main processing unit can be interfaced with a Bluetooth module to provide a suitable short range communication means (210). Also other technologies capable of obtaining the same result can be used such as ZigBee. In order to implement also tele-rehabilitation functionalities the apparatus must comprise long-range communication means (211) which allows the device to connect to a remote server to upload the collected data. To enhance usability the apparatus can embed a device which could support such functionality without relying on external devices such as PCs, routers, smartphones and so on. In a possible implementation the apparatus can hence embed a GPRS module, equipped with a SIM card, by which TCP/IP transaction over the Internet can be instantiated autonomously. The GRPS module can be interfaced via a standard communication port (209) to the MCU, which, in turn, manages its operation.

To enhance its usability the apparatus can be battery powered, avoiding the patients to deal with wiring the machine to the wall socket. To this aim a single power source, preferably a Li-Ion rechargeable battery, can be employed. The apparatus also comprises all the necessary circuitry to provide a stable voltage supply (i.e. voltage regulators) and manage the battery charge when a rechargeable battery is employed. In an exemplary implementation, monitoring circuitry to detect if the apparatus has little residual energy in the internal rechargeable battery should be included, along with a stabilized power supply for recharging the battery.

In the preferred embodiment all the devices apt to fulfill the functionalities described above can be embedded in a single printed circuit board, which in turn can be mounted inside the apparatus casing. The motherboard of the main processing unit preferably also hosts all the necessary connectors dedicated to wiring all the tools which cannot be embedded directly in the motherboard itself. All the wires should be kept hidden under the machine panels or where not possible should be adequately protected in order to prevent damages and to improve the patient safety.

Low Level Firmware

A first low level firmware is the one loaded onto the microcontroller hosted on the PCB in charge of enabling finger tapping exercises (S5 in FIG. 1), which takes care of managing both the scan of each sensible area present and the measurement of the time associated to each charge or discharge cycle performed during the scan. In the preferred embodiment (FIG. 12) the firmware lets the microcontroller stay in its idle state (100) until a request from the I2C bus master is received (101). The request triggers the scan of each sensible area and the measurement of the associated discharge time. The MCU charges one finger pad at the time (102) and waits its discharge in an idle state (103). When the sensible pad is discharged an interrupt is issued by the general purpose port to which the same pad is connected (104). The interrupt awakens the MCU from the idle state (103) and triggers the reading of the count value of a dedicate timer to obtain the discharge time (105). In this way it is possible to detect a high capacitance value associated with that sensible area (e.g. when the discharge time exceeds a predetermined threshold). The cycle is repeated for each sensible area present in the PCB (106). Consequently the status word can be created (107) by setting high the bits corresponding to the pads where a touch is detected. The status word can be then forwarded over the I2C bus (107). The firmware hence enters again the idle status (100), waiting for a new request from the I2C master.

The operation of the MCU of the main processing unit (FIG. 13) is controlled by another firmware loaded onto its flash memory. This firmware takes care of the system initialization, rehabilitation session management and signal processing and data forwarding to a remote device. In the following a possible implementation of this firmware will be depicted, considering the preferred embodiment where a low power microcontroller (MCU) is used. In a first phase all the internal and external peripherals must be set up for the operation. For energy efficiency reasons, to preserve battery life, the MCU operation is triggered by asynchronous interrupt service routines (ISR) issued by external events, while the MCU stays in energy saving mode (or low power mode LPM). All the resources present on the board, as conditioning stages, but also the MCU of the (S5) tool and communication modules, are held in reset when not needed. The device firmware should provide for managing the device in the two operating modes (1) and (2) addressed.

Figure 15:
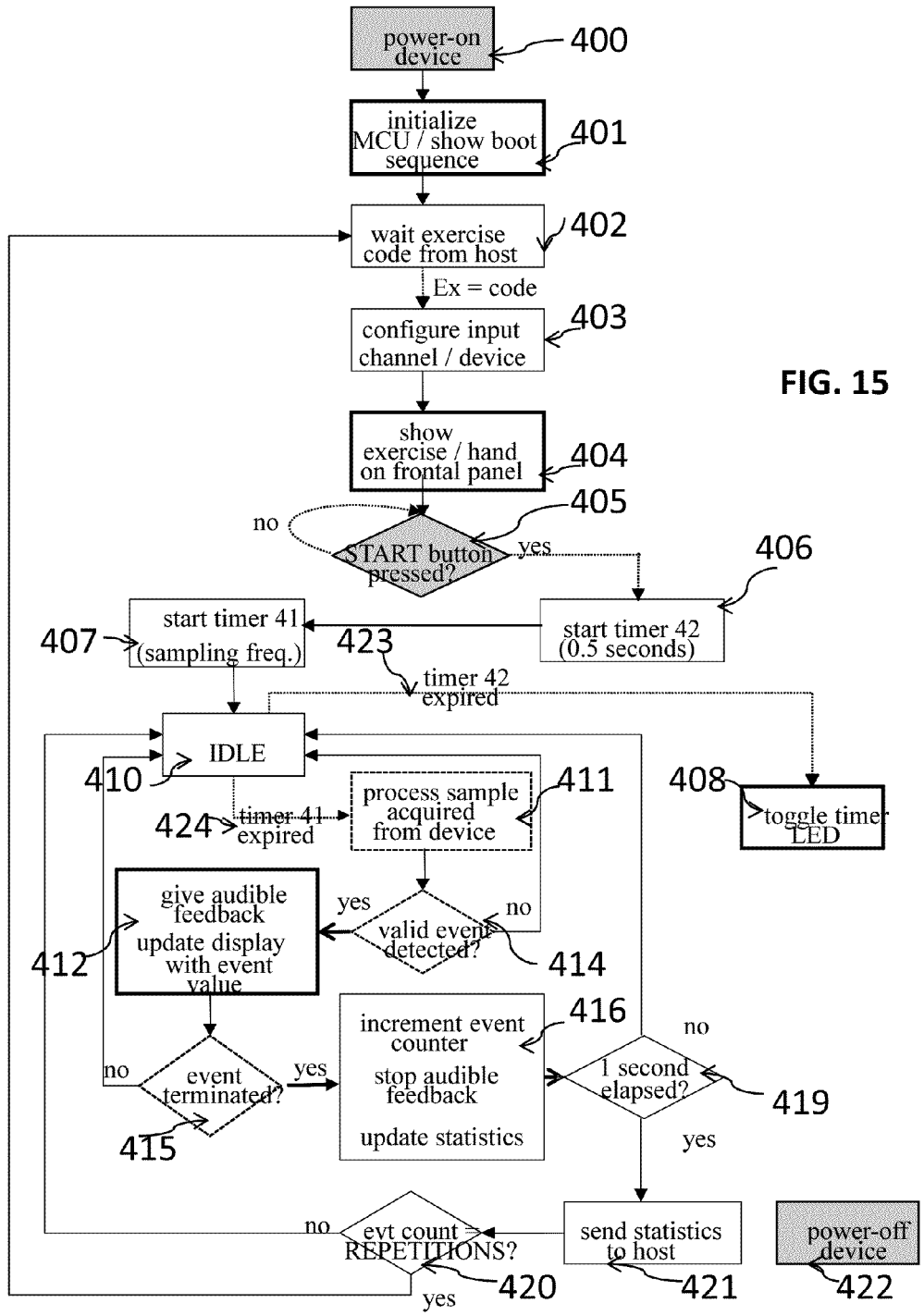

In an exemplary implementation (FIG. 15) the presence of the short-range communication module can be checked in order to initiate the real-time control mode. In this case the firmware operates within an endless loop, where each iteration corresponds to the execution of an entire exercise. After powering-up the device (400), the MCU initializes all the internal and external peripherals and shows to the user a visual boot-up sequence (401). Inside the loop the MCU goes immediately in LPM, waiting to receive the execution code of the exercise to launch (402). Depending on the selected exercise, some initializations are carried out (403), the ADC input channel is set to the corresponding signal conditioning stage output and it is started (except for the exercise involving S5), also showing on the visual feedback devices (P1) the indications on the exercise to execute (404). After that, the MCU goes in LPM again (405) so the patient can begin preparing himself for the first repetition according to the gym tool in use (in order to enable the auto-zero and other self-tuning operations in the apparatus), then starting the exercise on the apparatus with the specific button (P8), which in turns unlocks the execution (405).

Two different timers are started, the first used to beat the sampling frequency (407), the second to beat the reference time shown by the visual feedback device P4 (406). The MCU then stays in an idle state (410), from which it is awakened by the expiration of the aforementioned timers. When the second timer (timer 42) expires (423), the feedback device used to give a temporal reference is toggled (408). When the first timer (timer 41) expires (424) a new sample is received, a global counter is incremented, to keep track of the number of samples gathered and hence to extract time measurements from it. Then the actual signal processing takes place on a sample-by-sample basis, in different ways depending on the specific exercise (411). The outcome of the signal processing routine is checked (414) in order to recognise if a valid event has been detected. If so, the MCU sets the appropriate outputs to deliver the visible and audible (412) feedbacks to the patient.

When a valid event has been detected, the outcome of the signal processing routine is checked in order to recognise the termination of the event (415) and to stop correspondingly delivering the feedback signals (416). Hence the characteristics quantities extracted by the processing algorithm are validated and the statistics related to the whole exercise are updated. The current sample is sent to the host machine through the Bluetooth link, and as an example every second (150 samples) a vector containing statistics which characterize the execution is sent too, only if at least one new event has been registered during the last second (419). After sending the statistics vector over the Bluetooth link (421), the MCU checks if the stop condition which identifies the end of an exercise is met (420). If the verification fails, the core enters the LPM again from which it will be released by the acquisition of a new sample (410), otherwise the processing steps back to the main loop (402), entering in LPM until the system gets triggered again from the GUI. The power off of the device is asynchronous with respect to the flow described above and can happen at any time (422).

The second operating mode (2) is run when no short-range communication device is detected at power-up. In this case the system must be able to run the rehabilitation session autonomously, instructing the patient on which exercise to perform. The exercises to be run and the number of repetitions within each one are part of the rehabilitation protocol coded onto the firmware and stored onto the device flash memory. Such a protocol can be remotely upgraded if needed. The device operation proceeds similarly to mode (1) aside from the facts that the exercises are run automatically and that neither the acquired samples nor the intermediate statistics are sent during the training execution.

Figure 16:
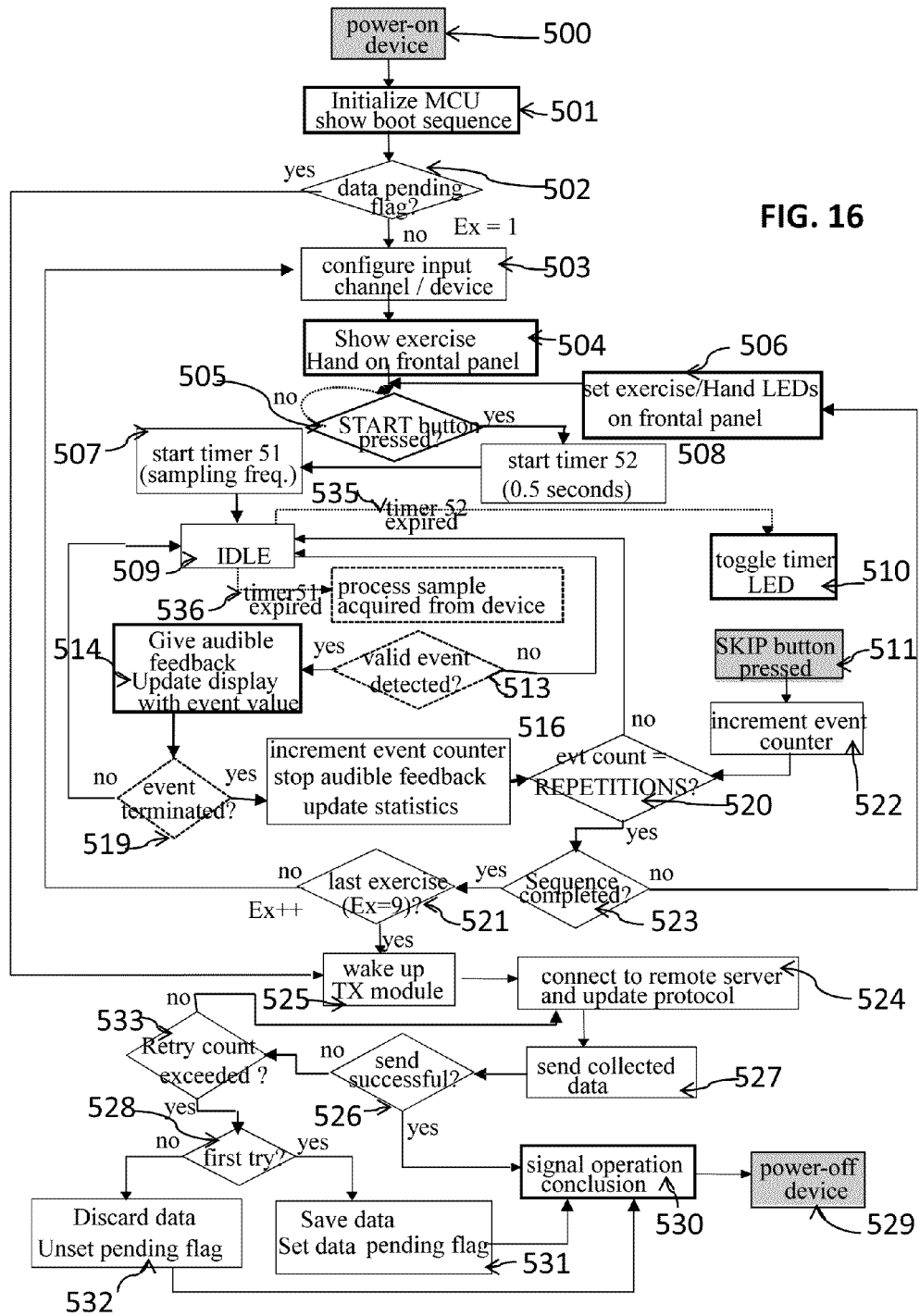

In an exemplary implementation (FIG. 16) the collected features are buffered on the local memory and stored until the training session is completed. Hence after powering up the device (500) the system modules are initialized and the visual feedback interface is activated to show a boot sequence (501). Then the MCU checks if the flash memory contains old data to be sent (502) and if the corresponding flag is set, the firmware jumps to transmitting said data (525). Otherwise the first exercise to be launched is set and the corresponding peripherals, such as timers, ADC, conditioning stage, are configured (503).

Subsequently the tools included in the visual feedback interface are set appropriately, showing which exercise is to be executed and which hand the patient must use (504). At this point the MCU goes in LPM (505) so the patient can begin preparing himself for the first repetition according to the gym tool in use (in order to enable the auto-zero and other self-tuning operations in the apparatus), and waits for the start signal (505) coming from the specific button (P8), which in turns unlocks the execution.

Two different timers are started, the first used to beat the sampling frequency (507), the second to beat the reference time (508) shown by the visual feedback device (P4). The MCU stays in an idle state (509), from which it is unlocked by the expiration of the aforementioned timers. When the second timer (timer 52) expires (535), the feedback device (P4) used to give a temporal reference is toggled (510). When the first timer (timer 51) expires (536) the ADC is triggered in order to convert a new sample. Then the actual signal processing takes place on a sample-by-sample basis, in different ways depending on the specific exercise (512). The outcome of the signal processing routine is checked (513) in order to recognise if a valid event has been initiated. If so, the MCU sets the appropriate outputs pins to deliver the visible and audible (514) feedbacks to the patient.

From now on the outcome of the signal processing routine is checked in order to recognise the termination of the same event (519). When this step yields a positive result the MCU provides for stopping delivering the feedback signals (516). Hence the event characteristic quantities (such as amplitude, duration and so on) extracted by the processing algorithm are validated and the statistics related to the exercise execution are updated with the new values. It is then checked if the number of registered events equals the number of scheduled repetitions (520). If not, the MCU goes back to the idle state (509) and the processing is repeated until the patient performs the requested number of actions (i.e. repetitions) on the gym tool.

The MCU execution flow can be asynchronously unlocked from the idle state (509) also by the patient pressing the (P9) button. This starts a routine which increments the number of repetitions registered (522), without altering either the collected statistics or the number of valid events. When the condition (520) is met other tests are performed in order to detect if the number of sequences to be performed is reached (523) and if the exercise to be performed are completed (521). In both cases if the test fails the number of sequences/exercise is incremented and the processing flow is repeated starting from the exercise setup phase by updating only the visual feedback interface if the exercise is not completed (506) or by setting the device properly for a new exercise (503).

When the training is completed the device firmware triggers the long-range communication module (525) and establishes a TCP/IP connection with the remote server (524). When the apparatus is connected to the remote server (524), it downloads the new protocol if available, as set by the therapist in order to upgrade it as from the evidences of the analysis of the rehabilitation progress. Subsequently it sends a chunk of data composed of a header and a payload (527). The header is a unique identifier of the device, while the payload is the vector of the training session statistics, in binary format. The amount of data sent is constant, regardless of the actual rehabilitation protocol configuration (the areas corresponding to non-executed exercises are zero-padded), and so it is easy to identify the data of a given exercise simply relying on their position into the frame.

The MCU then waits for the server acknowledgement message (526). As the latter is received the apparatus signals to the user the positive conclusion of the transaction (530), meaning that it can be turned off (529). If the operation is not completed successfully the number of attempts is checked (533) to verify if a predefined threshold of trials is reached. If not the execution flow steps back to connecting to the server (524) and a new transmission attempt is performed.

If none of the trials are successful, the MCU checks (528) whether the data have been just collected or if they come from a previous training session and were stored onto the flash memory. In the first case the data are saved onto the flash memory (531) and the visual feedback is set to notify the operation conclusion along with the failure condition met (530). Also the data pending flag is set in order to trigger the data transmission at the next starting of the device. In this way it is possible to recover the data after an unsuccessful transaction due, for example, to a momentary GSM network malfunctioning. In the second case, in order to avoid an endless loop, the data are discarded (532) and the operation result is notified (530) to the patient.

Processing Algorithms

In the following a possible implementation is described of the processing algorithms running on the apparatus and designated to detect the patient's action on the tools and to extract the performance characteristics. For all the exercises but the one involving S5, the samples can be first low-pass filtered by an 8-tap moving average filter in order to further smooth the signal.

Figure 17:
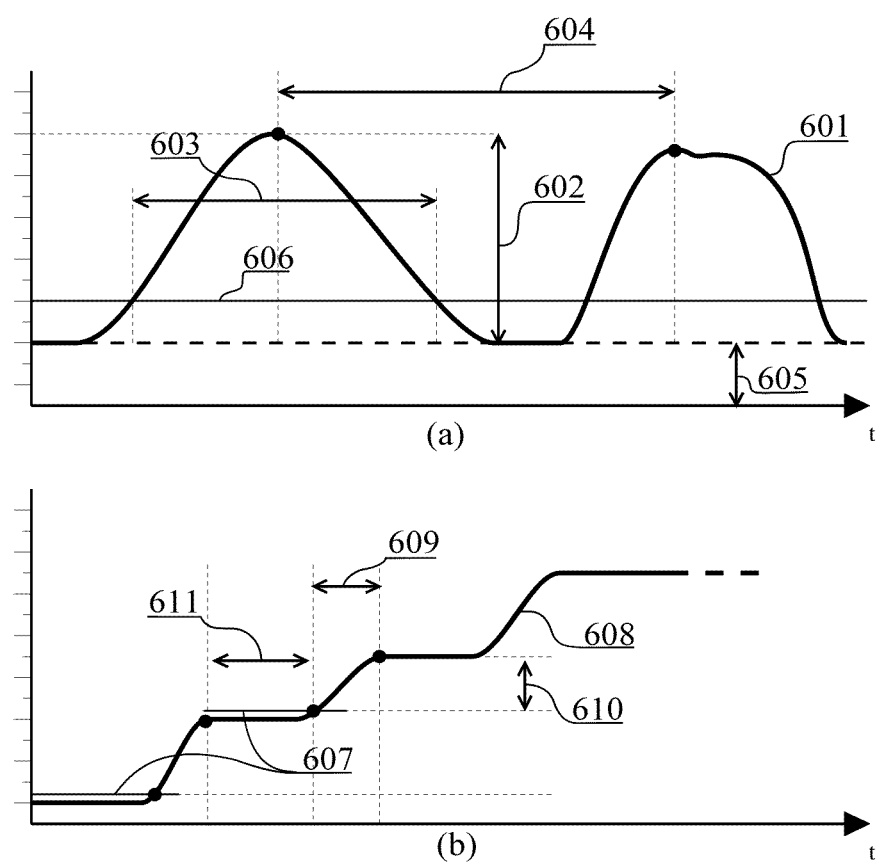
FIGS. 17a, 17b show exemplary embodiments of the time diagrams of the processing algorithms of the apparatus of the present invention.

Different algorithms must be used in correspondence of different signals. In an exemplary embodiment of the present invention, the included tools can produce up to 4 different signals. A peak-shaped waveform characterizes both signals coming from the force and linear position sensors (FIG. 17a). This first algorithm (A) detects the signal peaks corresponding respectively to a hand extension or a force application. This is done by comparing each sample with a threshold (606), correspondent to the minimum effort allowed. All the values are referred to a zero represented by the initial condition of the sensorized tool when the user is ready to start (605). The peak event is validated only if at least 75 consecutive samples are above the threshold and only as soon as the samples go under the threshold again. The peak maximum value (602), its duration (603) and position are determined and used to compute their incremental mean values as:

$$m_n = (m_{n-1} \times (n-1) + s) \div n$$

where $m_n$ is the mean value computed over n samples, and s is the value of the last peak (its maximum). The apparatus also stores the absolute maximum and minimum values for the peaks amplitude within an exercise repetition, along with the distance between two consecutive peaks (604). To characterize the obtained average value also the variance $\sigma^2$ can be computed incrementally:

$$M_n = (M_{n-1} \times (n-1) + s^2) \div n,$$

$$\sigma^2 = M_n - (m_n \times m_n)$$

The whole set of parameters extracted incrementally plus the individual features of each peak can be sent to the therapist's personal computer when the device is operating in mode (1), while preferably only a summary of the same statistics (Table 1), the number of repetitions executed could be stored and sent over the internet when operating in mode (2).

TABLE 1

| Algorithm | Parameters | AverageValue | Std. deviation | Max/Min |
|---|---|---|---|---|
| A | Peaksamplitude | yes | yes | yes |
|   | Peaksduration | yes | yes | no |
|   | Peaksdistance | yes | no | no |

TABLE 1-continued

| Algorithm | Parameters | AverageValue | Std. deviation | Max/Min |
|---|---|---|---|---|
| B | Rotation angle | yes | yes | no |
|   | Rotationspeed | yes | yes | no |
| C | Temperature | no | no | no |
| D | Duration of all sequences | yes | no | no |
|   | Duration of correct sequences | yes | no | no |
|   | Consecutive touchesspeed | yes | no | no |

In the case of the dynamic rotation exercise (involving S6) different features are extracted by a second algorithm (B) (FIG. 17b), primarily related to rotation angle, rotation speed. The typical signal has a terraced waveform (608), where the edges correspond to the rotations whereas the plateaus indicate no actions on the tool. The duration of both edges (609) and plateaus (611), and the amplitude of each edge (610), are extracted. To detect both onset and end of an edge, a detection mechanism based on thresholds has been designed, exploiting the smoothness of the filtered signal. A FIFO buffer of 14 samples is linearly updated at every new sample. The mean value of the oldest 4 samples is computed and compared with the most recent sample. If the difference is greater than an empirically determined threshold, the algorithm detects an edge and marks the onset at the index of the central sample of the buffer. When the difference falls back under the current threshold, the edge end is marked and the processing is repeated, until the potentiometer reaches the limit. By using absolute values, the processing can be employed in correspondence of both clockwise and counter-clockwise rotations. As with algorithm A the incremental average value and variance of the quantities of interest can be computed incrementally. Both individual values and incremental statistics can be sent along with the acquired signal to the therapist's PC when operating in mode (1), while preferably only the extracted statistics (Table 1), along with the number of rotations performed and the total duration of the exercise can be sent to the remote server for deferred monitoring (2), separately for clockwise and anti-clockwise rotations.

The signal coming from the hand temperature detection sensor is a slowly varying signal proportional to the temperature value detected. A correspondent algorithm (C) aims to recognise when the acquired signal has become stable and to extract the temperature value. To this aim a FIFO buffer of 16 samples is updated whenever a new sample is received and all the elements are compared with the oldest one. If the difference between every sample and the oldest one is under a threshold, the signal is considered stable and the average value of the 16 buffered values is computed as representative of the temperature value. In both operating modes the values enabling the temperature computing with the interpolating Steinhart-Hart equation are sent to the host machine.

In correspondence of the S5 tool there are no analogue signals involved. Another algorithm (D) runs on the main MCU and processes the 8-bit word provided by the S5 tool whenever requested in order to detect the correct execution of a sequence. As a new word is received, it is mirrored, if necessary, in order to have the least significant bit always referred to the thumb key. When the first not null data is received, the algorithm detects the less significant bit set to 1 and creates a mask used, at the next touch, to check if the next key tapped corresponds to a less significant bit or not. If this is true, the mask is updated and the processing goes on, otherwise an error flag is set. The sequence terminates when the thumb touch is detected (lsb=1). If the number of touches is equal to five, the valid sequence counter is incremented or, if either the error flag is set or the sequence length differs from five, the bad sequence counter is. This processing is performed in real-time and, when the exercise is complete, an additional routine computes the relevant statistics, including average duration of the correct sequences, consecutive touch speed, average duration of all sequences (correct and wrong), and total duration of the exercise. In the same way as the other algorithms preferably only the exercise statistics (and the number of correct and wrong sequences) (Table 1) are sent to the remote server when mode (2) is used, whereas also the partial data are sent over the short-range link with the therapist's PC (1).

Real-Time Monitoring Software

In conjunction with the operating mode (1), relating to a first example of embodiment of the system according to the invention, by using a graphical user interface software application tool running on his PC the physician can monitor in real-time the execution quality of the kinesitherapic exercises, also extracting useful information to evaluate the rehabilitation progress over time. As already said, the link between the apparatus and the host PC can be based on one of the short-range communication technologies available (i.e. Bluetooth, ZigBee).

Figure 18:
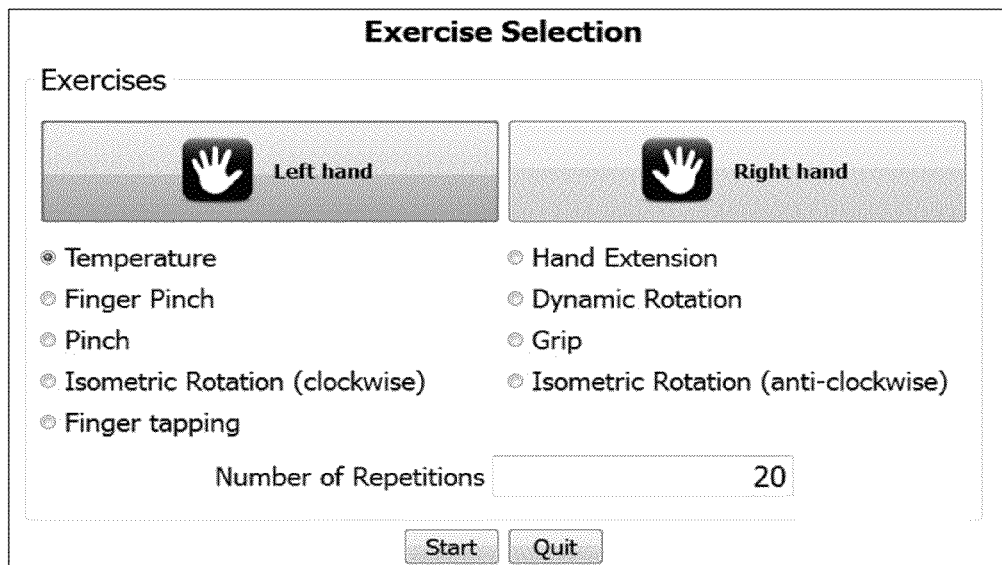
FIGS. 18 to 21 show exemplary embodiments of displaying windows for control of the apparatus and results of the real time processing of the apparatus of the present invention.
Figure 19:
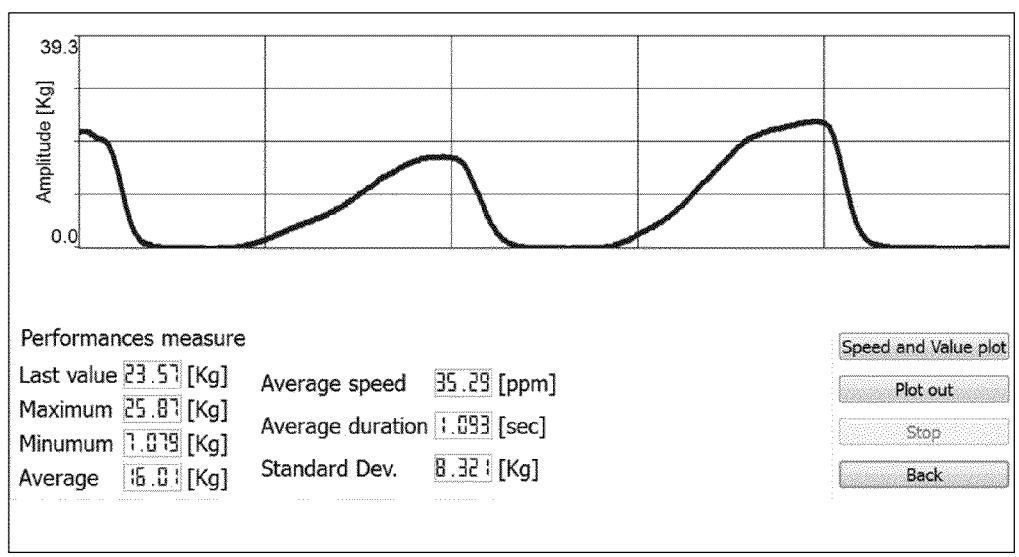
Figure 20:
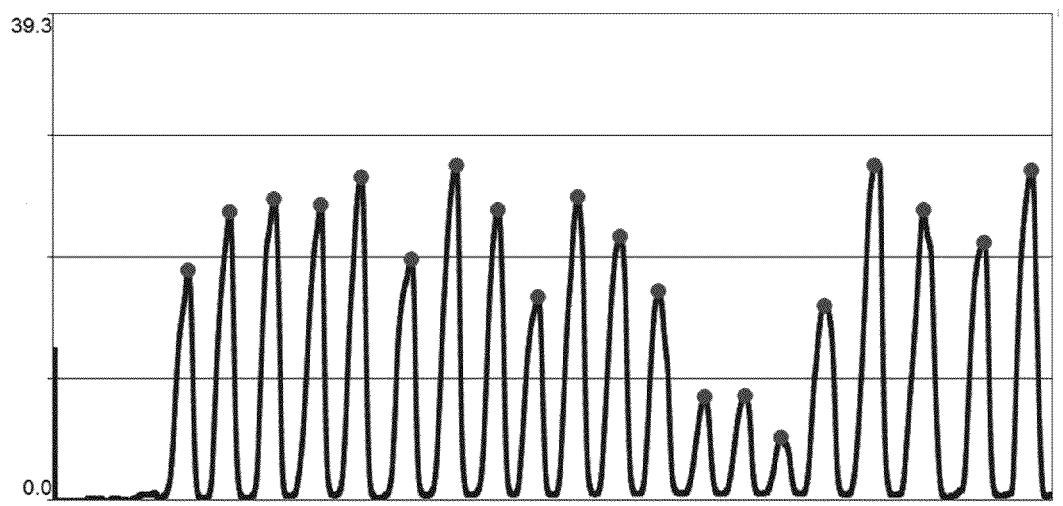

At launch, the very first window containing a list of radio buttons enables the selection of the exercise and the hand to use and the number of repetitions to perform (FIG. 18). By pushing the start button on the GUI, a numerical code which identifies the chosen exercise and the hand to use can be sent to the device. The call-back function associated to this button creates a new window which is specific for the selected exercise. The exercise window preferably includes an area where the raw signal acquired by the sensor can be displayed over time and a set of text boxes where the statistics can be shown (FIG. 19). The signal is sent to the host PC on a sample-by-sample basis. The received samples are then converted to the corresponding real physical quantity by means of calibration values. All the received samples can be logged thus, at the end of the execution, the user can visualize a static plot of the whole signal along with the markers used by the apparatus in the segmentation process (FIG. 20). The plot of the whole signal can be usefully exploited for defining the thresholds of minimum and maximum load for any given exercise.

Figure 21:
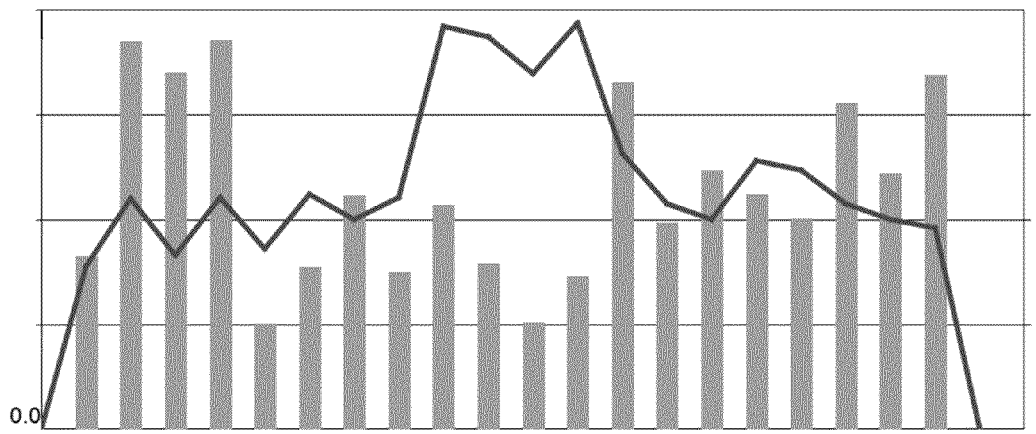

The GUI can also receive the peaks position detected in real-time by the apparatus along with the other relevant parameters extracted (e.g. speed of execution, amplitude of the last peak, the maximum, the minimum and the average values registered). These statistics can be sent by the apparatus to the host PC only every 150 samples of the signal and can be used to update the correspondent text boxes on the GUI. The end of the exercise could be signalled by the device to the software by means of a flag at the end of the data chunk. The interface can use this flag to enable the visualization of the whole signal plot, including the markers to the peaks found by the apparatus during the execution. Also the visualization of the "speed-value plot" (FIG. 21) can be unlocked simultaneously. The latter overprints to a bar graph showing the peak values a line graph representing the frequency of the repetitions. This information can be useful to evaluate how much the performance is dependent by the execution speed, being important to know if smaller values achieved by the patient are caused by a higher execution speed or by fatigue.

In every moment the therapist is able to stop the execution. For example in correspondence of the pressure of a push button a numerical code could be sent to the device in order to signal the premature end of the exercise. Another push button enables going back to the main window, where the user can select a new exercise.

The Remote Server

Figures 22, 23:
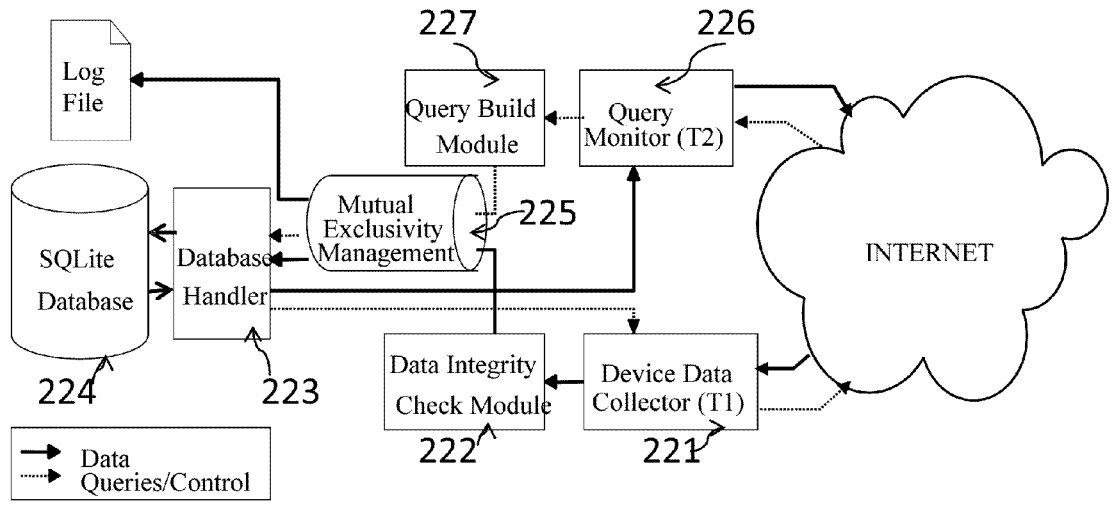

In order to exploit the proposed invention as a tele-rehabilitation support tool, relating to a second example of embodiment of the system according to the invention, a remote server application responsible of collecting the data from the rehabilitation kits and of storing them in a database for an easy retrieval, is preferably included. In the following a possible implementation of such an application is described. The remote software can be developed by means of one of the available high level programming languages such as C, C++, Java as well as by means of other scripting languages specifically targeted to web applications such as php or html. In an exemplary embodiment a C++ based implementation is considered. The software is able both to collect and store the data coming from the rehabilitation devices and to process and to answer the requests forwarded by the therapist's software monitoring tool (FIG. 22).

The application listens continuously for incoming connections, ready to receive new data at any time (allowing the patients to have no time schedule for their training sessions). For an improved efficiency the different functionalities, such as taking care of the data traffic from/to both ends of the apparatus (i.e. from patients' apparatuses and from physicians' PCs) can be handled by two parallel threads (T1 and T2), each one listening on a different socket for incoming connections.

The first one 221 (T1) is the interface towards the rehabilitation apparatuses. When a new connection is requested, T1 creates a parallel thread which handles the transfer while it continues to listen for incoming connection, allowing multiple transactions to be handled simultaneously. The incoming data frame must be accepted, temporarily stored and parsed. The frame header containing the apparatus identifier reveals which registered apparatus is sending the data. If a valid device is recognised the fixed sized data frame must be analysed to check the data integrity by the DataIntegrityCheck module 222. An error can be logged if: the client apparatus is not recognised, an insufficient amount of data has been received, the received data integrity check fails. A list of events occurred upon an unsuccessful connection can be stored in a log file without inserting any data into the database. After a successful validation, an acknowledgement message can be sent to the apparatus, allowing the connection to be terminated. Hence the data can be inserted into the database by the Database Handler module 223. Although the server manages multiple connections at the same time, for example thanks to a multithreaded approach, to avoid corrupting the database integrity, all the operations performed on the shared resources must be mutually exclusive. A dedicated software module can be responsible of ensuring that only one thread at the time accesses the database or the log file, for example by exploiting mutexes (which implements mutual exclusivity) or semaphores 225.

The interface towards the monitoring application can be handled by a different module running on a parallel thread T2. It is capable of collecting the messages sent by the monitoring application, which basically contain different parameters (such as date, patient IDs, exercise IDs), which isolates different sets of data in the database, and to answer with the appropriate data. The QueryMonitor module 226 can also be in charge of managing a security mechanism like authenticated access. Upon successful authentication, the received parameters can be sent to a separate module (QueryBuilder 227), which builds the correspondent SQL query and issues it to the Database Handler. If any results are found on the database, the Database Handler module 223 packs them and forwards a single data frame to the QueryMonitor 226, which in turn sends it back to the monitoring application.

The server application must host locally a database 224 to store orderly the patients' historical data. In a preferred embodiment a relational database could be used, exploiting one of the existing technologies in the field. For example a SQLite database can be employed. This choice eases the apparatus design, being not necessary the adoption of a database manager. Still it can be accessed by means of standard SQL queries and all its contents reside on a single file, which can be backed-up easily for safety reasons. The database structure can comprehend at least 4 tables: a table (D1) containing the list of registered devices, a table (D2) containing the list of the rehabilitation sessions recorded by the apparatus, a set of tables (D3) for each exercise containing the data related to the executions of that particular exercise by each patient, a table (D4) containing the rehabilitation protocol associated with each user.

D2 and D3 can be accessed by both the rehabilitation users (to insert the data) and the physician's monitoring software (read only, through the access queries). The latter can also modify D4 content. The format of the messages exchanged between the server and the client applications can be of a known type, as well as the messages containing the server answers which are formatted regardless of the query being answered to. Deleting entries from the database, when necessary, must be done at low level by issuing specific SQL queries by the apparatus administrator, in order to avoid accidental loss of data. To improve safety, a copy of the database can be automatically backed-up every day via one of the available transfer protocols (e.g. SFTP) on a safe computer machine. This avoids losing the data stored onto the server memory in case of accidental damages to the machine. Another possibility could be that of managing a RAID unit directly onto the server computer.

Tele-Rehabilitation Application Software.

The therapist must be able to access the data and to evaluate the patient performance by means of a software application, which can allow an easy visualization of each patient's data on an intuitive graphical user interface (GUI). The software must be oriented towards the achievement of flexibility both in terms of data management and analysis. A possible implementation of such a software tool could consist of a GUI with four windows dedicated to: customize the application settings, send a query to the remote server and download the data, check the patients compliance to the rehabilitation protocol, analyse with more detail the historic results achieved by each patient.

In order to ease the data retrieval, the user can select graphically in the download window (FIG. 23) the parameters of the query he wants to issue to the remote database.

Figures 24, 25:
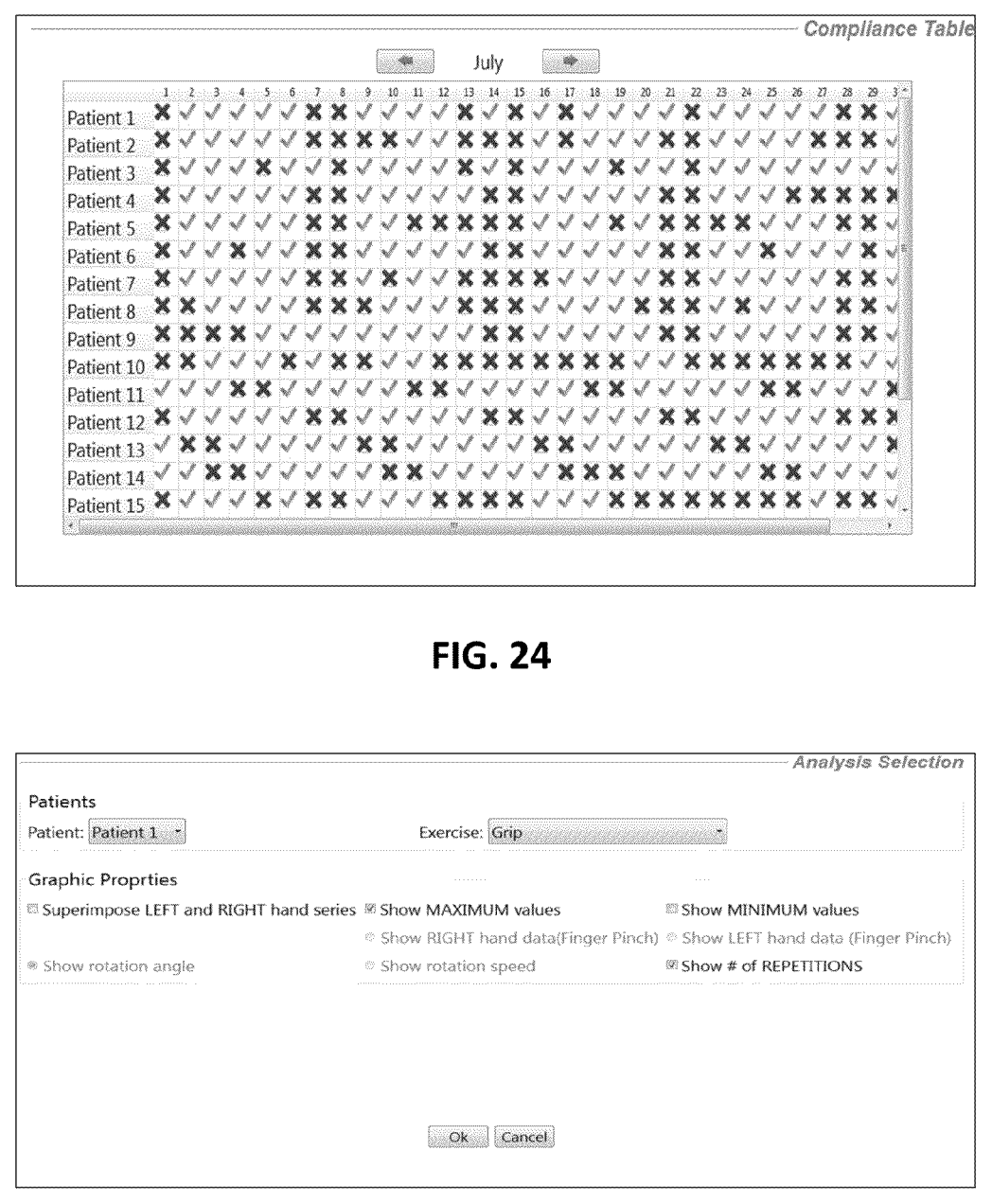

Once the data has been downloaded, the therapist has the possibility to perform different actions. It is possible to verify who is performing the training according to the protocol and who's not by means of the Compliance tab (FIG. 24). Here a table shows which patients do have a correspondent entry in the table D2 of the database (marked with a "v" which means that a patient did perform the training session that particular day) and which not (a cross is shown). This is a fast way to verify if some patients are not following the protocol correctly; the therapist can hence get in touch with them to find out if any problem has arisen.

Figure 26:
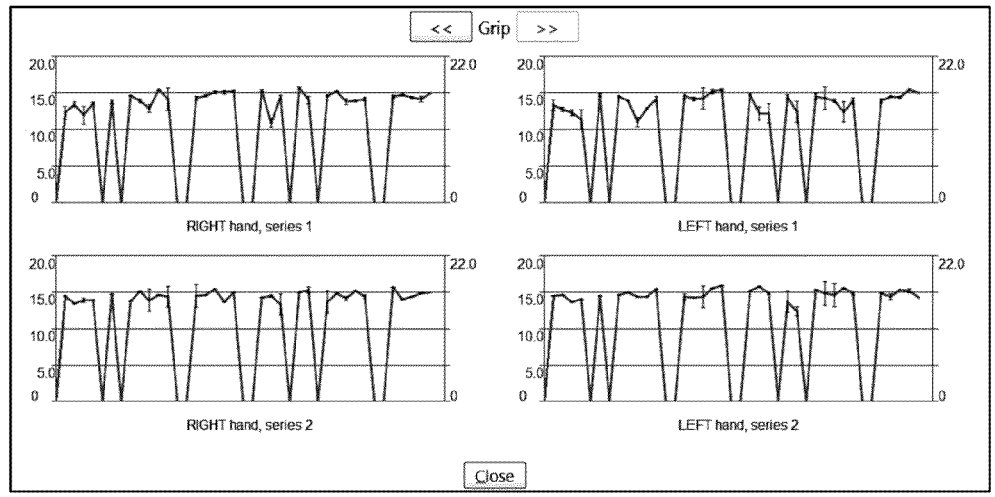
Figure 27:
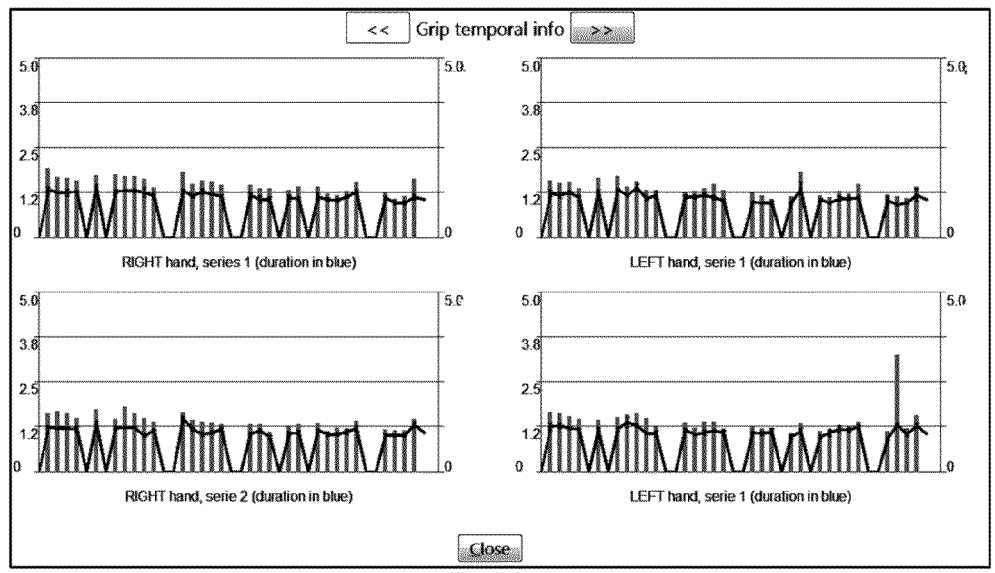
Figure 28:
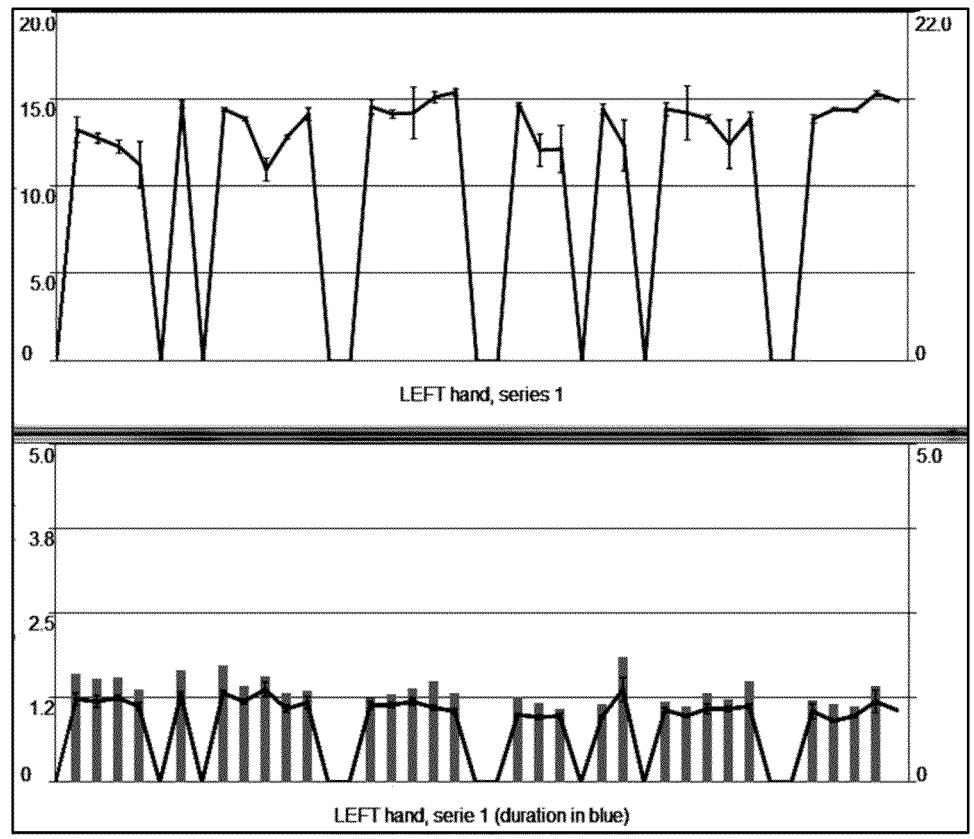
Figure 29:
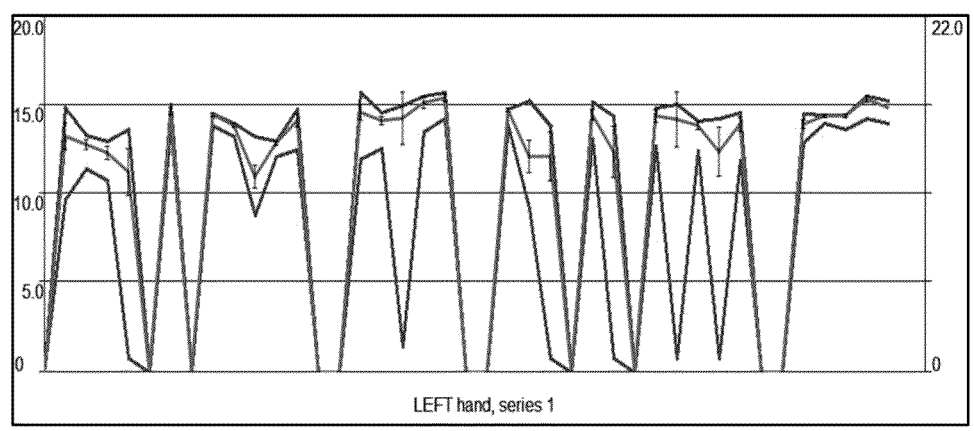

Also an immediate analysis of the patients' performance can be carried out and the data can be exported in a portable format (a .csv file for example) or saved locally for a delayed analysis. By means of the Analysis tab (FIG. 25), a more detailed analysis can be performed by selecting specific data subsets representative of the historic trend of each patient's performance in the individual exercises. The data are hence plotted on a time chart separately for each hand and series executed in the training sessions in the patient's specific window (FIGS. 26, 27). In the graphs, each point corresponds to the performance obtained by a patient in a given day. The performance is quantified approximately by the mean value of the physical quantity relevant for that exercise (e.g.: torque in Nm). The trend of this quantity gives a clue on the patient progresses. Further information such as maximum and minimum values, standard deviation and number of repetitions associated with each series are though necessary to assess the meaning of the mean value. The physician interface makes such data available in an intuitive and easily interpretable way, in order to ease performing such kind of analysis. For a fast comparison between the patients' performances and their associated temporal information the graphs can be detached from the main window and placed side by side (FIG. 28) or superimposed (FIG. 29). For a deeper insight, or statistical data characterization, the data can be exported in order to allow the exploitation of specific external software tools typically used in the medical community.

Methods

The different actors involved in the present invention are two: the therapist and the patient. The interaction between the two actors and between them and the tele-rehabilitation system built around the proposed apparatus are different in the two operating scenarios:

(1) real-time close distance control of the apparatus
(2) deferred telemonitoring with the apparatus The two scenarios and the involved parts of the proposed invention are described with reference to FIGS. 30 and 31.

The system basically comprises the apparatus 10 and a computer, i.e. a PC 321.

Figure 30:
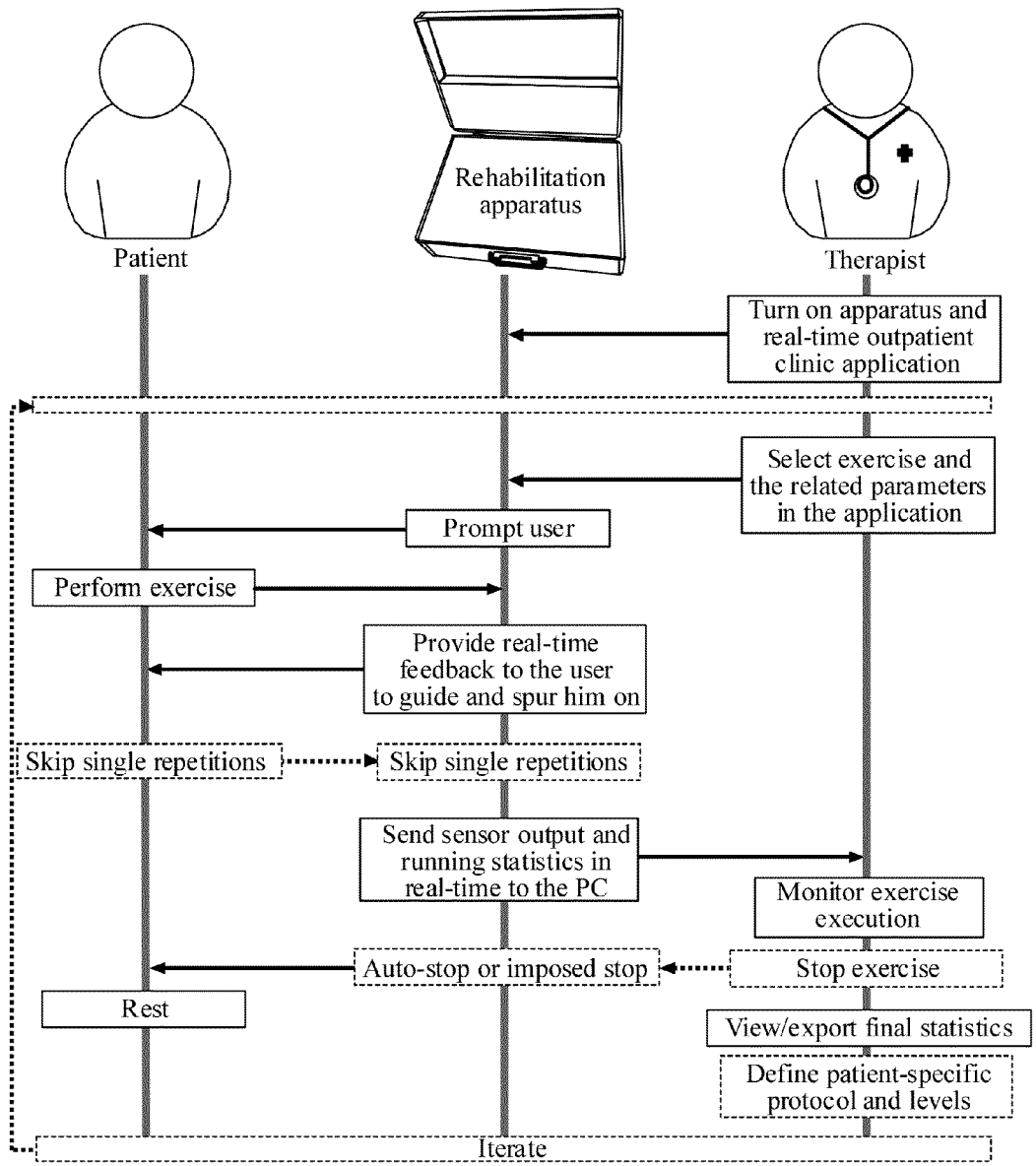
FIGS. 30 and 32 show respectively a logic flow-chart and hardware block diagram of a first alternative embodiment of real-time close distance control of the system of the present invention.
Figure 32:
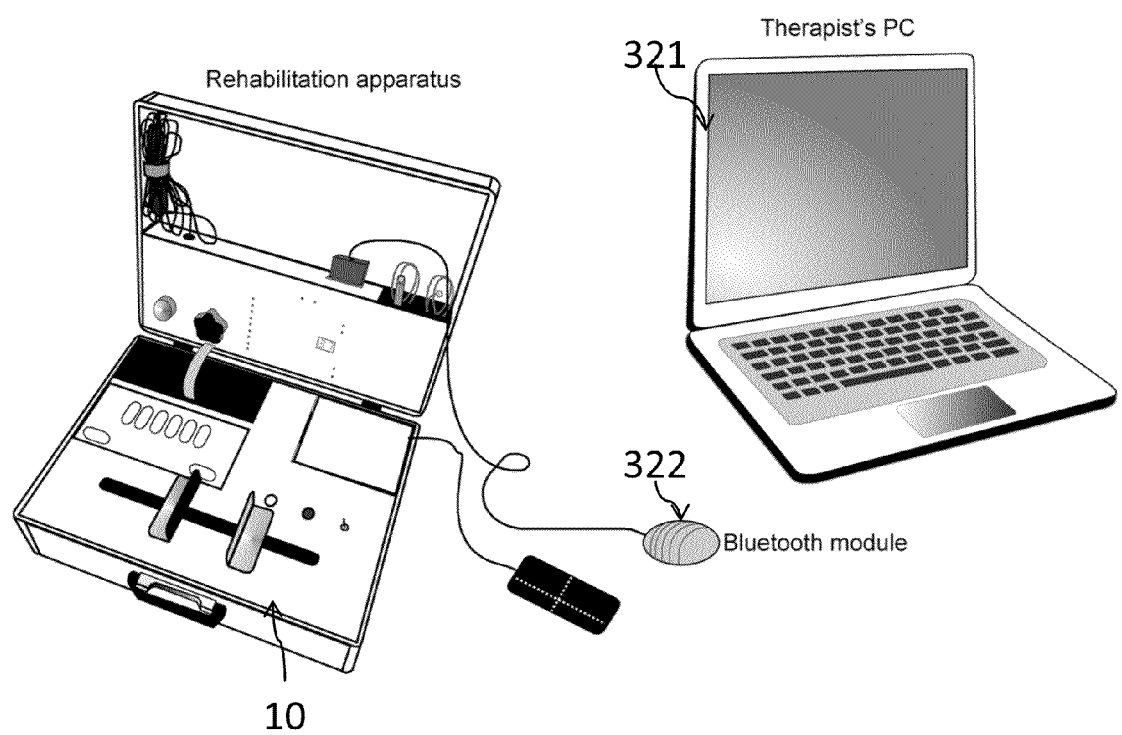

In case (1), FIGS. 30 and 32, it is assumed that the therapist is close to the patient, being able to talk with him, explain how the exercise must be performed and visually inspect the movements performed by the patient during the exercise. In this case, the therapist will connect an external Bluetooth module 322 to the apparatus to provide the short-range connectivity. The therapist can launch its outpatient clinic software application, by means of which he can control the apparatus operation and observe characteristics of the patient's performance in real-time. In this mode (1) the apparatus performs the real-time analysis of the incoming digitalized signals, extracting the relevant features (measurements on the signals) and computing the run-time statistics on them. The therapist should have the possibility of choosing a set of predefined thresholds identifying both the effectiveness of one repetition (an action above a minimum threshold) or the overshooting of the maximum effort accepted (action above a maximum threshold). The apparatus could provide different feedbacks to inform the patient about the progress of the current exercise.

This mode (1) of use is particularly useful for rehabilitation sessions in presence of a therapist or for the evaluation of a patient in an outpatient clinic, when it is necessary to have representative numbers of the patient's performance in every exercise under controlled conditions. The waveform of the signal coming from the apparatus can be used for advanced analysis of the movement. In an exemplary use case, where a grip exercise is included, it would be possible to evaluate the time needed to exert the maximum force, the duration of the sustained grip, the slope of the force during this time, the duration of the release phase, etc. Such aspects are particularly useful when evaluating patients with neurodegenerative diseases, particularly Parkinson and Multiple Sclerosis. All the acquired data can be saved in ascii format for subsequent analysis in external programs or for filing purposes.

The flow-chart of FIG. 30 shows a detailed representation of an example of the sequence of logic operations of the software governing the way of working in the real-time close distance control of the apparatus in the scenario (1): the Figure is fully representative without any need of further explanation.

Figure 31:
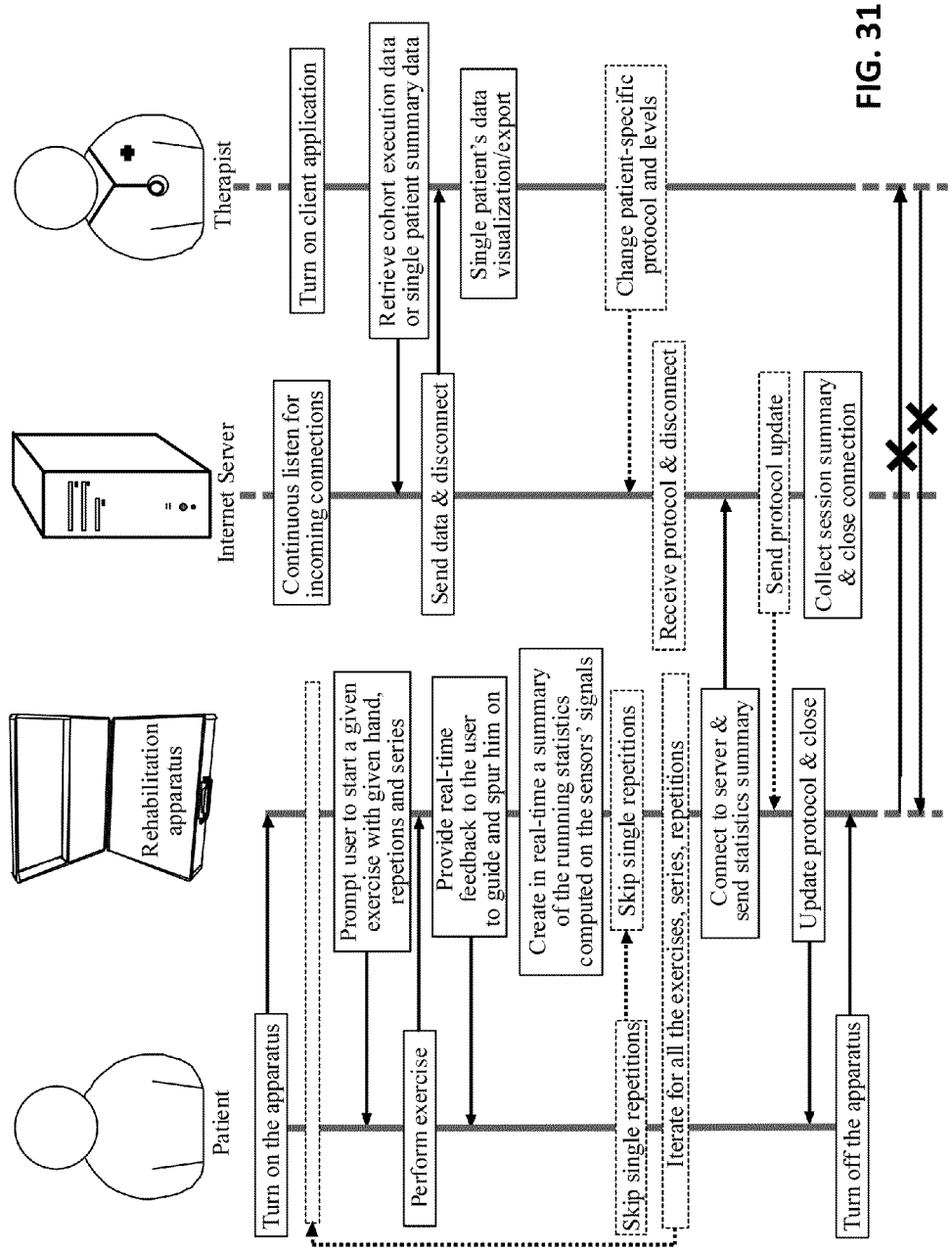
FIGS. 31 and 33 show respectively a logic flow-chart and hardware block diagram of a second alternative embodiment of deferred tele-monitoring control of the system of the present invention.
Figure 33:
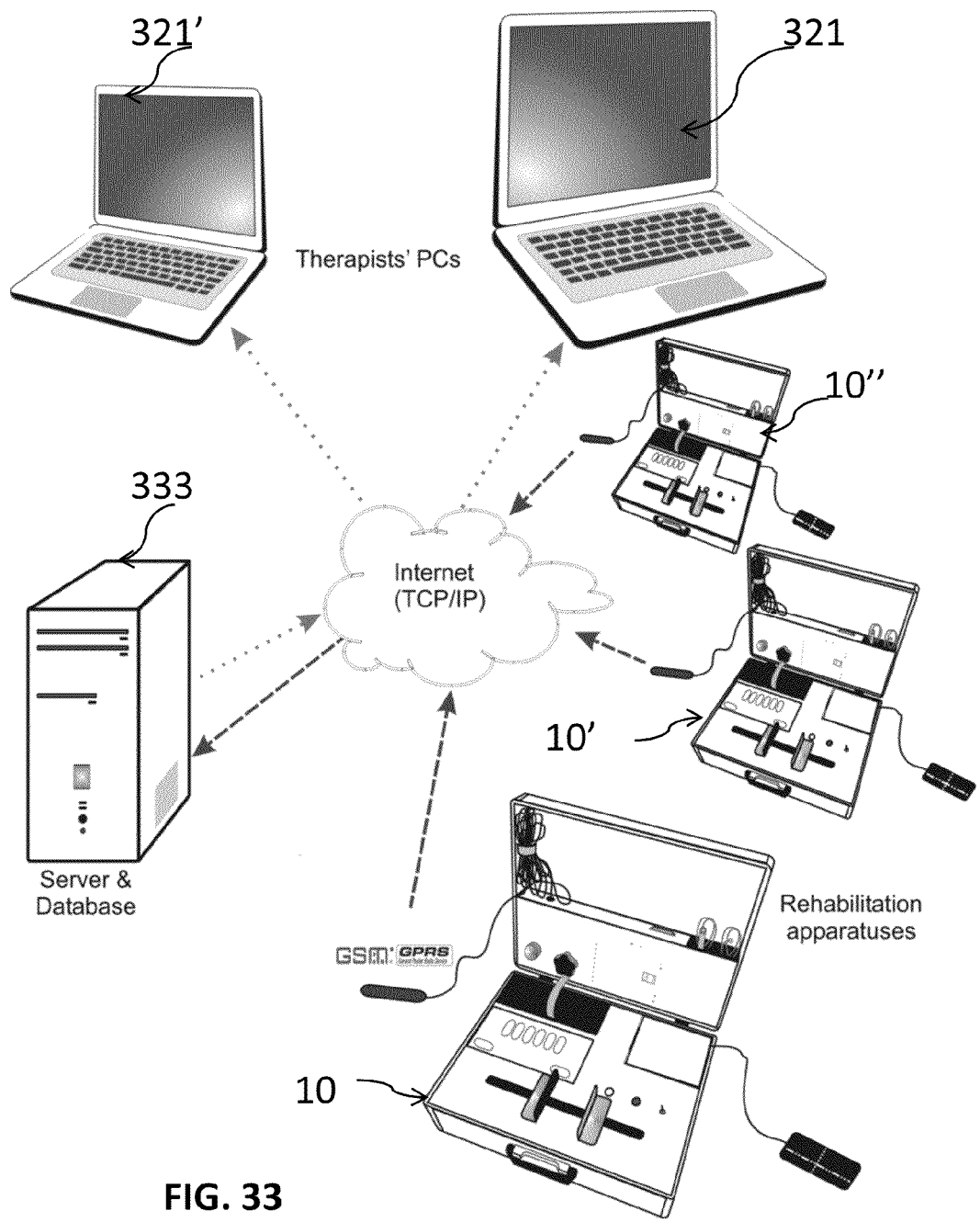

In case (2), FIGS. 31 and 33, the system basically comprises one or more apparatuses (10, 10', 10"), one or more computers (321, 321'), a server 333, with connections through a communication network like Internet.

It is assumed that the therapist is not close to the patient, who is performing the rehabilitation session on his own, with his own apparatus. At power on, an apparatus prompts the user with the first exercise, indicating the exercise name, the hand to use and the number of the series to be performed by means of the equipped visual interface. Now the patient interacts with the apparatus in the same way as in case (1), receiving feedbacks about his performance and the progress of the exercise. During the training at home, such feedbacks are particularly important for the patient since the therapist is not following in real-time the rehabilitation session and then it is necessary to have a method for enhancing the compliance of the patient to the rehabilitation protocol, at the same time providing an interactive experience able to stimulate the patient (compared to passive mechanical rehabilitation tools). During a series, if the patient feels pain, discomfort or is not able to proceed in the exercise, he can skip a single repetition or to abort the exercise in order to move on with the training session.

As said, during the series execution, the apparatus extracts from the signals coming from the sensors equipping the sensorized gym tools the relevant features after a segmentation of the raw signal, and computes the running statistics on them. While in this operating mode, the raw signal is discarded (conversely to mode (1)), the final statistics are preserved so that at the end of the whole rehabilitation session, the apparatus automatically sends them to the server over the internet. The adoption of an internal GSM/GPRS module (or equivalent) allows the easy management of the connection costs by the health care provider, regardless the place where actually the rehabilitation sessions take place. The summary of the rehabilitation session enables a deferred analysis by the therapist on both the quality of the performed exercise and the progress of the rehabilitation over the days.

In this scenario (2), the therapist is an actor who operates asynchronously with respect to the patient. In fact the therapist is never directly involved in the rehabilitation session while it is in progress, in this operating mode. The therapist, after a proper training of the patients in person, operates only through a client software application. The main roles of the therapist in this operating mode are:

setting up the rehabilitation protocol and, using a client application, loading it into the remote server for deferred upload of the rehabilitation apparatuses. To this aim the therapist will use a simple graphical user interface in order to define the new protocol. Such new choice will take effect only after the next connection of the desired apparatus to the server;

downloading and viewing the rehabilitation summaries for given patients, exploiting the client application, and having a global view of the adhesion to the rehabilitation program by all the monitored patients. To this aim, the client application is able of downloading the execution data, reporting with different symbols the days when the rehabilitation program has been performed and those when not. An automatic compliance monitor could be easily set up in order to automate this phase. Then, for a selected patient, it is possible to see the trend of any of the features extracted by the apparatus and summarized for every rehabilitation session.

analyzing the obtained data in order to evaluate the progress of the patients in the rehabilitation, the quality of the individual rehabilitation sessions, possible modifications to the rehabilitation protocol. The therapist can use such information also to provide suggestions to the patients in order to achieve better results. The time series discussed above, related to the same exercise but reporting different physical quantities, can be jointly analyzed for better explaining some phenomena. Furthermore the same time series obtained from the summaries for a given patient can be automatically analyzed with the help of an expert system or an artificial intelligence tool in order to speed up the telemonitoring process when the number of patients is high, defining a set of warning messages catching the attention of the therapist only for those patients whose time series present abnormal behaviors (either individually or coupled, as exemplified before). E.g. if the trend of the grip force is decreasing over time (every sample in time being a day of rehabilitation) it could be possible that the patient is performing the exercise faster than before, which can be easily discovered looking at the time series related to the frequency of the repetitions or to the duration of every grip movement. Otherwise it is possible that the patient is improperly using the feedback on the minimal threshold to limit his effort in the exercise, or possibly the patient is experiencing some troubles. In any case, the therapist can get in touch with the patient to find the real reasons of the observed behavior. The presence of a short summary of the rehabilitation sessions allows the therapist to track the progress of the different patients with good level of detail, without overwhelming information hardly usable when the number of patients grows.

The flow-chart of FIG. 32 shows a detailed representation of an example of the sequence of logic operations of the software governing the way of working in the deferred telemonitoring with the apparatus in the scenario (2): the Figure is fully representative without any need of further explanation.

Obviously the experts in the field could find many variations to the embodiment herein described, still within the scope of the present invention.

What is claimed is:

1. An apparatus for the local and/or remote rehabilitation and functional evaluation of the right and/or left hand of a user, the apparatus comprising:

a number of gym tools for the execution of hand exercises, each gym tool including a mechanical part and a sensor for the transformation of measured physical parameters into electrical signals;

a user interface, configured to guide the user in the use of said gym tools, and providing feedbacks to the sequence of user actions;

a first processing unit, configured to manage the apparatus functions, signal processing, storing and forwarding information on said measured physical parameters to at least one external device;

a short-range communication module, configured to allow a real-time close-distance control of the apparatus;

a wide-range communication module, configured to allow the connection to at least one long-distance tele-monitoring system;

wherein said number of gym tools comprise:
   a temperature sensor of fingers;
   a first gym tool configured for identification of the pinch strength of each finger in opposition to the thumb of the hand;
   a second gym tool configured for identification of lateral extension of the hand on a plane;
   a third gym tool configured for identification of an hand agility when executing a sequence of touches of fingers on a plane;
   a fourth gym tool configured for identification of an hand agility when rotating a handle without using a wrist;
   a fifth gym tool configured for identification of an hand pinch and grip strength;
   a sixth gym tool configured for identification of an hand torque when rotating a fixed handle without using a wrist.

2. The apparatus of claim 1, wherein said third gym tool is configured for identification of an hand agility when executing a sequence of touches of fingers on a plane comprises:
   a capacitive touch board, including a number of key-shaped sensible areas arranged to be both-hand usable, configured so as to provide a detection of the touch of fingers and to avoid direct current injection in the hand;
   a managing unit configured so as to:
      manage the reading of the capacitance associated to said key-shaped sensible areas, by sequentially charging said areas and measuring the discharge time, in presence and absence of finger touches;
      recognize valid or bad sequences of touches.

3. The apparatus of claim 1, wherein said user visual interface comprises:
   a set of visual indicators showing which exercise to execute, the right or left hand to use, the series of repetitions to perform, a blinking time reference, a low battery condition;
   interaction switches and/or buttons configured so as to allow to start or stop exercises, to skip single or multiple repetitions of exercises.

4. The apparatus of claim 1, wherein said first processing unit is configured to operate said sensors for the transformation of measured physical parameters into electrical signals, said sensors comprising implementation angle, distance, force, position, temperature, torque, touch sensors, so as to determine one or more of the following parameters, concurring to compose said information on said measured physical parameters:
   peak-shaped waveform characterizing signals coming from force and linear position sensors corresponding to a hand extension or a force application, determining peak maximum value, duration and time position;
   rotation angle, rotation speed characterizing signals coming from dynamic rotation sensors, said signals having terraced waveforms where edges correspond to rotations and plateaus indicate no actions on the tool, extracting duration of both edges and plateaus, and the amplitude of each edge;
   temperature values coming from the hand temperature detection sensor;
   sequence duration and speed of consecutive touches, average touch duration for each finger, average distance between them, total consecutive touches and total duration of the exercise, in said sequence of touches of fingers on a plane.

5. The apparatus of claim 4, wherein said first processing unit is configured so as to:
   determine said parameters on peak maximum value, duration and time position of said peak-shaped waveform characterizing signals by calculating the respective running statistics such as average values and variances;
   compute the absolute maximum and minimum values for the peaks amplitude within an exercise repetition, the number of repetitions along with the said statistical representative values computed on amplitudes, peak duration and distance between peaks for peak-shaped signals;
   calculate the total duration and the number of rotations performed in an exercise, along with the said statistical representative values computed on rotation angle and rotation speed, separately for clockwise and anti-clockwise rotations for signals having terraced waveforms.

6. A system for the local and/or remote rehabilitation and functional evaluation of the right and/or left hand of a user, the system comprising an apparatus comprising:
   a number of gym tools for the execution of hand exercises, each gym tool including a mechanical part and a sensor for the transformation of measured physical parameters into electrical signals;
   a user visual interface, configured to guiding the user in the use of said gym tools, and providing feedbacks to the sequence of user actions;
   a first processing unit, configured to manage the apparatus functions, signal processing, storing and forwarding information on said measured physical parameters to at least one external device;
   a short-range communication module, configured to allow a real-time close-distance control of the apparatus;
   the system also comprising at least one second processing unit, in said at least one external device, configured to interact with said short-range communication module, for said real-time close-distance control of the apparatus;
   wherein:
      said first processing unit is configured to operate said sensors for the transformation of measured physical parameters into electrical signals, as said information on said measured physical parameters, said sensors comprising implementation angle, distance, force, position, temperature, torque, touch sensors;
      said at least one external device comprises a graphical user interface tool configured so as: to receive and display said information on said measured physical parameters; to monitor in real-time the execution quality of said exercises; to enable selection of the gym tool to be used and the number of repetitions of the exercises to be performed; to stop executions of said exercises.

7. A system for the local and/or remote rehabilitation and functional evaluation of the right and/or left hand of a user, the system comprising at least one apparatus comprising:
   a number of gym tools for the execution of hand exercises, each gym tool including a mechanical part and a sensor for the transformation of measured physical parameters into electrical signals;
   a user visual interface, configured to guiding the user in the use of said gym tools, and providing feedbacks to the sequence of user actions;

a first processing unit, configured to manage the apparatus functions, signal processing, storing and forwarding statistical information on said measured physical parameters to at least one external device;

a wide-range communication module, configured to allow the connection to at least one long-distance tele-monitoring system;

the system also comprising said at least one long-distance tele-monitoring system comprising:

at least one server configured to store said statistical information on said measured physical parameters;

at least one second processing unit, in said at least one external device, configured to interact with said at least one server, for said long-distance tele-monitoring;

wherein:

said first processing unit is configured to operate said sensors for the transformation of measured physical parameters into electrical signals, as said information on said measured physical parameters, said sensors comprising implementation angle, distance, force, position, temperature, torque, touch sensors;

said at least one external device comprises a graphical user interface tool configured so as: to receive and display said statistical information on said measured physical parameters; to perform said long-distance tele-monitoring of the execution quality of said exercises.

8. The system of claim 7, wherein said at least one server is configured for:

receiving the connections from apparatuses assigned to different users, storing said statistical information, and sending to said apparatuses an upgrade of a rehabilitation protocol;

receiving queries for a deferred retrieval of user data, and for managing client application upgrades on rehabilitation protocols for specific users;

providing data for a deferred monitoring application on said at least one second processing unit, in order to evaluate compliance of the users to the assigned protocol, visualize the history of said statistical information, analyze achieved results, modify and upgrade said rehabilitation protocol for a specific user.

9. The system of claim 8, wherein said at least one server is configured for comprising a database structure with:

a first table containing a list of registered apparatuses;

a second table containing a list of the rehabilitation sessions recorded by apparatuses;

a set of tables for each exercise containing the data related to the executions of that particular exercise by each user;

a third table containing the rehabilitation protocol associated with each user.

10. A method for the local and/or remote rehabilitation and functional evaluation of the right and/or left hand of a user, the method comprising the steps of:

providing a number of gym tools for the execution of hand exercises, each gym tool including a mechanical part and a sensor for the transformation of measured physical parameters into electrical signals;

providing a user visual interface, configured to guiding the user in the use of said gym tools, and providing feedbacks to the sequence of user actions;

performing a first processing, to manage the functions of the gym tools, signal processing, storing and forwarding information or statistical information on said measured physical parameters to at least one external device;

performing a short-range communication, to allow a real-time close-distance control of the method;

performing a wide-range communication, to allow the connection to at least one long-distance tele-monitoring system;

wherein said first processing operates said sensors for the transformation of measured physical parameters into electrical signals, so as to determine one or more of the following parameters, concurring to compose said information or statistical information on said measured physical parameters:

peak-shape waveform characterizing signals coming from force and linear position sensors corresponding to a extension or a force application, determining peak maximum value, duration and time position;

rotation angle, rotation speed characterizing signals coming from dynamic rotation sensors, said signals having terraced waveforms where edges correspond to rotations and plateaus indicate no actions on the tool, extracting duration of both edges and plateaus, and the amplitude of each edges;

temperature values coming from the hand temperature detection sensor;

sequence duration and speed of consecutive touches, average touch duration for each finger, average distance between them, total consecutive touches and total duration of the exercise, in said sequence of touches of fingers on a plane.

11. The method of claim 10, comprising the steps of:

providing at least one second processing, in said at least one external device, to interact with said short-range communication, for said real-time close-distance control of the method.

12. The method of claim 10, comprising the steps of:

providing at least one server to store said statistical information on said measured physical parameters;

providing at least one second processing, in said at least one external device, to interact with said at least one server, for said long-distance tele-monitoring.

13. The method of claim 10, wherein said first processing operates so as to:

determine said parameters on peak maximum value, duration and time position of said peak-shaped waveform characterizing signals by calculating the respective running statistics such as average values and variances;

compute the absolute maximum and minimum values for the peaks amplitude within an exercise repetition, the number of repetitions along with the said statistical representative values computed on amplitudes, peak duration and distance between peaks for peak-shaped signals;

calculate the total duration and the number of rotations performed in an exercise, along with the said statistical representative values computed on rotation angle and rotation speed, separately for clockwise and anti-clockwise rotations for signals having terraced waveforms.

\* \* \* \* \*